United States Patent
Sheffer et al.

(10) Patent No.: US 8,571,637 B2
(45) Date of Patent: Oct. 29, 2013

(54) PATELLA TRACKING METHOD AND APPARATUS FOR USE IN SURGICAL NAVIGATION

(75) Inventors: Garrett Sheffer, Hoboken, NJ (US); Ryan Schoenefeld, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1212 days.

(21) Appl. No.: 12/356,963

(22) Filed: Jan. 21, 2009

(65) Prior Publication Data

US 2009/0183740 A1 Jul. 23, 2009

Related U.S. Application Data

(60) Provisional application No. 61/022,374, filed on Jan. 21, 2008.

(51) Int. Cl.
*A61B 5/11* (2006.01)
*A61B 5/05* (2006.01)

(52) U.S. Cl.
USPC ............ 600/424; 600/407; 600/426; 128/845

(58) Field of Classification Search
USPC .......... 128/845, 882; 600/407, 414, 424, 426, 600/459; 700/11–15, 17, 56–59; 434/267, 434/274; 606/130
See application file for complete search history.

(56) References Cited

U.S. PATENT DOCUMENTS

| | | |
|---|---|---|
| 4,341,220 A | 7/1982 | Perry |
| 4,360,028 A | 11/1982 | Barbier et al. |
| 4,583,538 A | 4/1986 | Onik et al. |
| 4,791,934 A | 12/1988 | Brunnett |
| 4,945,914 A | 8/1990 | Allen |
| 4,991,579 A | 2/1991 | Allen |
| 5,016,639 A | 5/1991 | Allen |
| 5,086,401 A | 2/1992 | Glassman et al. |

(Continued)

FOREIGN PATENT DOCUMENTS

| | | |
|---|---|---|
| EP | 0 427 358 A1 | 5/1991 |
| EP | 0 649 117 A2 | 4/1995 |

(Continued)

OTHER PUBLICATIONS

Muller PE, Pellengahr C, Witt M, Kircher J, Refior HJ, Jansson V. Influence of minimally invasive surgery on implant positioning and the functional outcome for medial unicompartmental knee arthroplasty. J Arthroplasty 2004; 19(3): 296-301.

(Continued)

*Primary Examiner* — Patricia Bianco
*Assistant Examiner* — Keri J Nelson
(74) *Attorney, Agent, or Firm* — Ryan O. White; Taft Stettinius & Hollister LLP

(57) ABSTRACT

An apparatus for use in tracking movement of a patella through a range of motion during a surgical navigation procedure, comprising a frame fixed in relation to the patella, a patella trial component associated with the frame for fixing the frame relative to the patella, and a reference array configured to attach to the frame, the reference array having first, second and third markers, the first, second and third markers being detectable by a surgical navigation system when exposed to a measurement field of the surgical navigation system.

7 Claims, 15 Drawing Sheets

(56) References Cited

U.S. PATENT DOCUMENTS

| | | |
|---|---|---|
| 5,094,241 A | 3/1992 | Allen |
| 5,097,839 A | 3/1992 | Allen |
| 5,119,817 A | 6/1992 | Allen |
| 5,142,930 A | 9/1992 | Allen et al. |
| 5,178,164 A | 1/1993 | Allen |
| 5,211,164 A | 5/1993 | Allen |
| 5,222,499 A | 6/1993 | Allen et al. |
| 5,230,338 A | 7/1993 | Allen et al. |
| 5,309,913 A | 5/1994 | Kormos et al. |
| 5,383,454 A | 1/1995 | Bucholz |
| 5,389,101 A | 2/1995 | Heilbrun et al. |
| 5,397,329 A | 3/1995 | Allen |
| 5,517,990 A | 5/1996 | Kalfas et al. |
| 5,603,318 A | 2/1997 | Heilbrun et al. |
| 5,628,315 A | 5/1997 | Vilsmeier et al. |
| 5,638,819 A | 6/1997 | Manwaring et al. |
| 5,682,886 A | 11/1997 | Delp et al. |
| 5,682,890 A | 11/1997 | Kormos et al. |
| D387,427 S | 12/1997 | Bucholz et al. |
| 5,732,703 A | 3/1998 | Kalfas et al. |
| 5,769,861 A | 6/1998 | Vilsmeier |
| 5,772,594 A | 6/1998 | Barrick |
| 5,776,064 A | 7/1998 | Kalfas et al. |
| 5,799,055 A | 8/1998 | Peshkin et al. |
| 5,836,954 A | 11/1998 | Heilbrun et al. |
| 5,851,183 A | 12/1998 | Bucholz |
| 5,871,018 A | 2/1999 | Delp et al. |
| 5,891,034 A | 4/1999 | Bucholz |
| 5,902,239 A | 5/1999 | Buurman |
| 5,967,982 A | 10/1999 | Barnett |
| 5,980,535 A | 11/1999 | Barnett et al. |
| 5,987,960 A | 11/1999 | Messner et al. |
| 5,999,837 A | 12/1999 | Messner et al. |
| 6,005,548 A | 12/1999 | Latypov et al. |
| D420,132 S | 2/2000 | Bucholz et al. |
| 6,021,343 A | 2/2000 | Foley et al. |
| D422,706 S | 4/2000 | Bucholz et al. |
| 6,050,724 A | 4/2000 | Schmitz et al. |
| 6,069,932 A | 5/2000 | Peshkin et al. |
| 6,096,050 A | 8/2000 | Audette |
| 6,122,541 A | 9/2000 | Cosman et al. |
| 6,161,033 A | 12/2000 | Kuhn |
| 6,166,746 A | 12/2000 | Inada et al. |
| 6,167,145 A | 12/2000 | Foley et al. |
| 6,167,292 A | 12/2000 | Badano et al. |
| 6,178,345 B1 | 1/2001 | Vilsmeier et al. |
| 6,187,018 B1 | 2/2001 | Sanjay-Gopal et al. |
| 6,190,395 B1 | 2/2001 | Williams |
| 6,198,794 B1 | 3/2001 | Peshkin et al. |
| 6,205,411 B1 | 3/2001 | DiGioia, III et al. |
| 6,235,038 B1 | 5/2001 | Hunter et al. |
| 6,236,875 B1 | 5/2001 | Bucholz et al. |
| 6,246,900 B1 | 6/2001 | Cosman et al. |
| 6,285,902 B1 | 9/2001 | Kienzle, III et al. |
| 6,306,126 B1 | 10/2001 | Moctezuma |
| 6,377,839 B1 | 4/2002 | Kalfas et al. |
| 6,379,302 B1 | 4/2002 | Kessman et al. |
| 6,381,485 B1 | 4/2002 | Hunter et al. |
| 6,402,762 B2 | 6/2002 | Hunter et al. |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,434,507 B1 | 8/2002 | Clayton et al. |
| 6,470,207 B1 | 10/2002 | Simon et al. |
| 6,477,400 B1 | 11/2002 | Barrick |
| 6,490,467 B1 | 12/2002 | Bucholz et al. |
| 6,490,475 B1 | 12/2002 | Seeley et al. |
| 6,490,777 B1 | 12/2002 | Proulx et al. |
| 6,491,699 B1 | 12/2002 | Henderson et al. |
| 6,493,574 B1 | 12/2002 | Ehnholm et al. |
| 6,507,751 B2 | 1/2003 | Blume et al. |
| 6,527,443 B1 | 3/2003 | Vilsmeier et al. |
| 6,535,756 B1 | 3/2003 | Simon et al. |
| 6,551,325 B2 | 4/2003 | Neubauer et al. |
| 6,553,152 B1 | 4/2003 | Miller et al. |
| 6,556,857 B1 | 4/2003 | Estes et al. |
| 6,584,174 B2 | 6/2003 | Schubert et al. |
| 6,609,022 B2 | 8/2003 | Vilsmeier et al. |
| 6,643,535 B2 | 11/2003 | Damasco et al. |
| 6,674,916 B1 | 1/2004 | Deman et al. |
| 6,697,664 B2 | 2/2004 | Kienzle III et al. |
| 6,714,629 B2 | 3/2004 | Vilsmeier |
| 6,718,194 B2 | 4/2004 | Kienzle, III |
| 6,724,922 B1 | 4/2004 | Vilsmeier |
| 6,725,080 B2 | 4/2004 | Melkent et al. |
| 6,725,082 B2 | 4/2004 | Sati et al. |
| 6,754,374 B1 | 6/2004 | Miller et al. |
| 6,772,002 B2 | 8/2004 | Schmidt et al. |
| 6,776,526 B2 | 8/2004 | Zeiss |
| 6,782,287 B2 | 8/2004 | Grzeszczuk et al. |
| 6,855,150 B1 | 2/2005 | Linehan |
| 6,856,826 B2 | 2/2005 | Seeley et al. |
| 6,856,827 B2 | 2/2005 | Seeley et al. |
| 6,856,828 B2 | 2/2005 | Cossette et al. |
| 6,887,245 B2 | 5/2005 | Kienzle, III et al. |
| 6,887,247 B1 | 5/2005 | Couture et al. |
| 6,892,088 B2 | 5/2005 | Faulkner et al. |
| 6,895,268 B1 | 5/2005 | Rahn et al. |
| 6,896,657 B2 | 5/2005 | Willis |
| 6,917,827 B2 | 7/2005 | Kienzle, III |
| 6,920,347 B2 | 7/2005 | Simon et al. |
| 6,925,339 B2 | 8/2005 | Grimm et al. |
| 6,926,673 B2 | 8/2005 | Roberts et al. |
| 6,932,823 B2 | 8/2005 | Grimm et al. |
| 6,947,582 B1 | 9/2005 | Vilsmeier et al. |
| 6,947,783 B2 | 9/2005 | Immerz |
| 6,950,689 B1 | 9/2005 | Willis et al. |
| 6,978,166 B2 | 12/2005 | Foley et al. |
| 6,988,009 B2 | 1/2006 | Grimm et al. |
| 6,990,220 B2 | 1/2006 | Ellis et al. |
| 7,008,430 B2 | 3/2006 | Dong et al. |
| 7,010,095 B2 | 3/2006 | Mitschke et al. |
| 7,104,996 B2 | 9/2006 | Bonutti |
| 2001/0007918 A1 | 7/2001 | Vilsmeier et al. |
| 2001/0011175 A1 | 8/2001 | Hunter et al. |
| 2001/0027271 A1 | 10/2001 | Franck et al. |
| 2001/0036245 A1 | 11/2001 | Kienzle, III et al. |
| 2001/0051881 A1 | 12/2001 | Filler |
| 2002/0077540 A1 | 6/2002 | Kienzle, III |
| 2002/0095081 A1 | 7/2002 | Vilsmeier |
| 2002/0151894 A1 | 10/2002 | Melkent et al. |
| 2002/0183610 A1 | 12/2002 | Foley et al. |
| 2002/0188194 A1 | 12/2002 | Cosman |
| 2003/0059097 A1 | 3/2003 | Abovitz et al. |
| 2003/0209096 A1 | 11/2003 | Pandey et al. |
| 2004/0015077 A1 | 1/2004 | Sati et al. |
| 2004/0030245 A1 | 2/2004 | Noble et al. |
| 2004/0073228 A1 | 4/2004 | Kienzle, III et al. |
| 2004/0087852 A1 | 5/2004 | Chen et al. |
| 2004/0097952 A1 | 5/2004 | Sarin et al. |
| 2004/0127788 A1 | 7/2004 | Arata |
| 2004/0143184 A1 | 7/2004 | Kienzle, III |
| 2004/0152970 A1 | 8/2004 | Hunter et al. |
| 2004/0169673 A1 | 9/2004 | Crampe et al. |
| 2004/0254454 A1 | 12/2004 | Kockro |
| 2004/0254771 A1 | 12/2004 | Riener et al. |
| 2004/0267242 A1 | 12/2004 | Grimm et al. |
| 2005/0015003 A1 | 1/2005 | Lachner et al. |
| 2005/0015005 A1 | 1/2005 | Kockro |
| 2005/0015022 A1 | 1/2005 | Richard et al. |
| 2005/0015099 A1 | 1/2005 | Momoi et al. |
| 2005/0020909 A1 | 1/2005 | Moctezuma de la Barrera et al. |
| 2005/0020911 A1 | 1/2005 | Viswanathan et al. |
| 2005/0021037 A1 | 1/2005 | McCombs et al. |
| 2005/0021039 A1 | 1/2005 | Cusick et al. |
| 2005/0021043 A1 | 1/2005 | Jansen et al. |
| 2005/0021044 A1 | 1/2005 | Stone et al. |
| 2005/0033117 A1 | 2/2005 | Ozaki et al. |
| 2005/0033149 A1 | 2/2005 | Strommer et al. |
| 2005/0038337 A1 | 2/2005 | Edwards |
| 2005/0049477 A1 | 3/2005 | Fu et al. |
| 2005/0049478 A1 | 3/2005 | Kuduvalli et al. |
| 2005/0049485 A1 | 3/2005 | Harmon et al. |
| 2005/0049486 A1 | 3/2005 | Urquhart et al. |

(56) References Cited

U.S. PATENT DOCUMENTS

| | | |
|---|---|---|
| 2005/0054915 A1 | 3/2005 | Sukovic et al. |
| 2005/0054916 A1 | 3/2005 | Mostafavi |
| 2005/0059873 A1 | 3/2005 | Glozman et al. |
| 2005/0075632 A1 | 4/2005 | Russell et al. |
| 2005/0080334 A1 | 4/2005 | Willis |
| 2005/0085714 A1 | 4/2005 | Foley et al. |
| 2005/0085715 A1 | 4/2005 | Dukesherer et al. |
| 2005/0085717 A1 | 4/2005 | Shahidi |
| 2005/0085718 A1 | 4/2005 | Shahidi |
| 2005/0085720 A1 | 4/2005 | Jascob et al. |
| 2005/0090730 A1 | 4/2005 | Cortinovis et al. |
| 2005/0090733 A1 | 4/2005 | Van Der Lugt et al. |
| 2005/0096515 A1 | 5/2005 | Geng |
| 2005/0096535 A1 | 5/2005 | de la Barrera |
| 2005/0101970 A1 | 5/2005 | Rosenberg |
| 2005/0113659 A1 | 5/2005 | Pothier et al. |
| 2005/0113960 A1 | 5/2005 | Karau et al. |
| 2005/0119561 A1 | 6/2005 | Kienzle, III |
| 2005/0119565 A1 | 6/2005 | Pescatore |
| 2005/0119639 A1 | 6/2005 | McCombs et al. |
| 2005/0119783 A1 | 6/2005 | Brisson et al. |
| 2005/0124988 A1 | 6/2005 | Terrill-Grisoni et al. |
| 2005/0137599 A1 | 6/2005 | Masini |
| 2005/0148850 A1 | 7/2005 | Lahm et al. |
| 2005/0148855 A1 | 7/2005 | Kienzle, III |
| 2005/0197568 A1 | 9/2005 | Vass et al. |
| 2005/0197569 A1 | 9/2005 | McCombs |
| 2005/0203373 A1 | 9/2005 | Boese et al. |
| 2005/0203374 A1 | 9/2005 | Vilsmeier |
| 2005/0203375 A1 | 9/2005 | Willis et al. |
| 2005/0203383 A1 | 9/2005 | Moctezuma de la Barrera et al. |
| 2005/0203384 A1 | 9/2005 | Sati et al. |
| 2005/0215879 A1 | 9/2005 | Chuanggui |
| 2005/0215888 A1 | 9/2005 | Grimm et al. |
| 2005/0216032 A1 | 9/2005 | Hayden |
| 2005/0228250 A1 | 10/2005 | Bitter et al. |
| 2005/0228266 A1 | 10/2005 | McCombs |
| 2005/0228270 A1 | 10/2005 | Lloyd et al. |
| 2005/0228404 A1 | 10/2005 | Vandevelde |
| 2005/0234335 A1 | 10/2005 | Simon et al. |
| 2005/0234465 A1 | 10/2005 | McCombs et al. |
| 2005/0251026 A1 | 11/2005 | Stone |
| 2005/0251030 A1 | 11/2005 | Azar et al. |
| 2005/0251065 A1 | 11/2005 | Henning et al. |
| 2005/0251113 A1 | 11/2005 | Kienzle, III |
| 2005/0261700 A1 | 11/2005 | Tuma et al. |
| 2005/0267353 A1 | 12/2005 | Marquart et al. |
| 2005/0267354 A1 | 12/2005 | Marquart et al. |
| 2005/0267358 A1 | 12/2005 | Tuma et al. |
| 2005/0267360 A1 | 12/2005 | Birkenbach et al. |
| 2005/0267365 A1 | 12/2005 | Sokulin et al. |
| 2005/0267722 A1 | 12/2005 | Marquart et al. |
| 2005/0277832 A1 | 12/2005 | Foley et al. |
| 2005/0279368 A1 | 12/2005 | McCombs |
| 2005/0281465 A1 | 12/2005 | Marquart et al. |
| 2005/0288575 A1 | 12/2005 | de la Barrera et al. |
| 2005/0288578 A1 | 12/2005 | Durlak |
| 2005/0288679 A1 | 12/2005 | Kienzle, III |
| 2006/0004284 A1 | 1/2006 | Grunschlager et al. |
| 2006/0009780 A1 | 1/2006 | Foley et al. |
| 2006/0015018 A1 | 1/2006 | Jutras et al. |
| 2006/0015030 A1 | 1/2006 | Poulin et al. |
| 2006/0015031 A1 | 1/2006 | Kienzle, III |
| 2006/0025677 A1 | 2/2006 | Verard et al. |
| 2006/0025679 A1 | 2/2006 | Viswanathan et al. |
| 2006/0025681 A1 | 2/2006 | Abovitz et al. |
| 2006/0036149 A1 | 2/2006 | Lavigna et al. |
| 2006/0036151 A1 | 2/2006 | Ferre et al. |
| 2006/0036162 A1 | 2/2006 | Shahidi et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0052691 A1 | 3/2006 | Hall et al. |
| 2006/0058604 A1 | 3/2006 | Avinash et al. |
| 2006/0058615 A1 | 3/2006 | Mahajan et al. |
| 2006/0058616 A1 | 3/2006 | Marquart et al. |
| 2006/0058644 A1 | 3/2006 | Hoppe et al. |
| 2006/0058646 A1 | 3/2006 | Viswanathan |
| 2006/0058663 A1 | 3/2006 | Willis et al. |
| 2007/0016008 A1* | 1/2007 | Schoenefeld ............... 600/424 |

FOREIGN PATENT DOCUMENTS

| | | |
|---|---|---|
| EP | 0 832 609 A2 | 4/1998 |
| EP | 0 904 735 A2 | 3/1999 |
| EP | 1 226 788 A1 | 7/2002 |
| GB | 2 246 936 | 2/1992 |
| WO | WO 94/17733 A1 | 8/1994 |
| WO | WO 95/15714 A1 | 6/1995 |
| WO | WO 02/35454 A1 | 5/2002 |
| WO | WO 02/062248 A1 | 8/2002 |
| WO | WO 02/067783 A2 | 9/2002 |
| WO | WO 2004/001569 A2 | 12/2003 |
| WO | WO 2004/006770 A2 | 1/2004 |
| WO | WO 2004/069036 A2 | 8/2004 |

OTHER PUBLICATIONS

Digioia AM, Jaramaz B; Colgan BD. Computer assisted orthopaedic surgery. Image guided and robotic assistive technologies. Clin Orthop Sep. 1998;(354):8-16.

David Stulberg S. How accurate is current TKR instrumentation? Clin Orthop. Nov. 2003;(416):177-84.

Bathis H, Perlick L, Tingart M, Luring C, Zurakowski D, Grifka J. Alignment in total knee arthroplasty. A comparison of computer-assisted surgery with the conventional technique. J Bone Joint Surg Br. 2004;86(5):682-687.

Chauhan SK, Clark GW, Lloyd S, Scott RG, Breidhal W, Sikorski JM. Computer-assisted total knee replacement: a controlled cadaver study using a multi-parameter quantitative CT assessment of alignment (the Perth CT Protocol). J Bone Joint Surg [Br] 2004;86-B:818-23.

James B. Stiehl et al., Navigation and Robotics in Total Joint and Spine Surgery, Chapter 3 C-Arm-Based Navigation, Springer-Verlag (2004) (9 pages).

Metzger, B. et al. "Patella Alignment and Tracking" Biomet, Inc. Brochure from website www.biomet.com, printed in 2007, 12 pages.

DiFranco. D.E. et al., "Recovery of 3D Articulated Motion from 2D Correspondences," Cambridge Research Laboratory Technical Report CRL 99/7, Dec. 1999 (20 pages).

James B. Stiehl et al., Navigation and Robotics in Total Joint and Spine Surgery, Chapter 1 Basics of Computer-Assisted Orthopedic Surgery (CAOS), Springer-Verlag (2004) (9 pages).

Donald G. Eckhoff, Joel M. Bch, Victor M. Spitzer, Karl D. Reinig, Michelle M. Bagur, Todd H. Baldini, David Rubinstein and Stephen Humphries, "Three-Dimensional Morphology and Kinematics of the Distal Part of the Femur Viewed in Virtual Reality. Part II," J Bone Joint Surg. Am 2003 85(Supp 4): 97-104.

Warfield, Simon: "Real-Time Image Segmentation for Image-Guided Surgery"; 14 pages; http://splweb.bwh.harvard.edu:8000/pages/papers/warfield/SC98/; accepted to appear at SC98, Nov. 1998.

Thomas C. Kienzle III, S. David Stulburg, Michael Peshkin, Arthur Quaid, Jon Lea, Ambarish Goswami, and Chi-Haur Wu: "A Computer-Assisted Total Knee Replacement Surgical System Using a Calibrated Robot," in "Computer-Integrated Surgery: Technology and Clinical Applications," ed. Russell H. Taylor, et al., 1996 MIT Press. (28 pages).

Luck, J.P., Debrunner, C., Hoff, W., He, Q., and Small, D. "Development and Analysis of a Real-Time Human Motion Tracking System," in *Proc. of Workshop on Applications of Computer Vision*. 2002. Orlando, FL, IEEE (7 pages).

Traxtal Technologies—Virtual Keypad, (printed May 23, 2005) pp. 1-2, http://www.traxtal.com/products/products_input_virtualkeypad.htm?print.

(56) References Cited

OTHER PUBLICATIONS

C. Graetzel, T.W. Fong, S. Grange, and C. Baur, "A non-contact mouse for surgeon-computer interaction," Technology and Health Care, vol. 12, No. 3, 2004, pp. 245-257.

Habets, R.J.E.: *Computer assistance in orthopaedic surgery*. Promoters: prof.dr.ir. A. Hasman, prof.dr.ir. F.A. Gerritsen; copromoter: dr.ir. J.A. Blom. Technische Universiteit Eindhoven, ISBN 90-386-1940-5, Nov. 4, 2002. (4 pages).

Visarius H, Gong J, Scheer C, Haralamb S, Nolte LP, Man-machine interfaces in computer assisted surgery. Comput Aid Surg 1997;2:102-107.

McPherson EJ (2006) Patellar tracking in primary total knee arthroplasty. Instr Course Lect 55:439-448.

Inoue, M., Shino, K., Hirose, H., Hirobe, S. & Ono, K., 1988. *Subluxation of the patella*. Journal of Bone and Joint. Surgery, 70, 1331-1337.

Lombardi, A.V. Jr.; Engh, G.A.; Volz, R.; Albrigo, J.L.; Brainard, B.J.: Fracture/dissociation of the polyethylene in metal-backed patellar components in total knee arthroplasty. The Journal of Bone and Joint Surgery, 70-A(5):675-679, Jun. 1988.

Grelsamer, RP: Patellar Malalignment—Current Concepts. J Bone Joint Surg. 82A:1639-1650, 2000.

Merkow R, Soudry M, Insall J: Patellar dislocation following total knee replacement. J Bone Joint Surg. 67A:1321, 1985.

Sven Ostermeier, et al. Dynamic in vitro measurement of patellar movement after total knee arthroplasty: an in vitro study, BMC Musculoskelet Disord. 2005; 6: 30.

\* cited by examiner

PATELLA TRACKING METHOD AND APPARATUS FOR USE IN SURGICAL NAVIGATION

RELATED APPLICATIONS

This application claims priority to U.S. Provisional Patent Application Ser. No. 61/022,374 filed Jan. 21, 2008, the disclosure of which is expressly incorporated by reference herein.

FIELD OF THE INVENTION

The present teachings relate generally to surgical navigation and more particularly to patella tracking components, as well as to methods for using such components to track a patella during a surgical navigation procedure.

BACKGROUND

Surgical navigation systems, also known as computer assisted surgery and image guided surgery systems, aid surgeons in locating patient anatomical structures, guiding surgical instruments, and implanting medical devices with a high degree of accuracy. Surgical navigation has been compared to global positioning systems, which aid vehicle operators as they navigate the earth. A surgical navigation system typically includes a computer, a tracking system, and patient anatomical information, The patient anatomical information can be obtained by using an imaging mode such as fluoroscopy, computer tomography (CT) or simply by defining locations on the patient's anatomy with the surgical navigation system. Surgical navigation systems can also be used for a wide variety of surgeries to improve patient outcomes.

To implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical navigation procedure, surgeons often utilize "tracking arrays," which are coupled to the surgical components. These tracking arrays allow the surgeon to accurately track the location of the surgical components, as well as the patient's bones during the surgery. By knowing the physical location of the tracking array, the tracking system's software is able to detect and calculate the position of the tracked component relative to a surgical plan image.

To replace a worn or damaged knee during a total knee arthroplasty ("TKA") procedure, a significant amount of effort is typically devoted to ensuring that the patient's knee is balanced. As part of this knee balancing process, it is important to make sure that the patella is properly aligned with the femur, particularly as a misaligned patella can cause poor leg motion and premature failure of the corrected knee. Procedures for tracking a patella with surgical navigation, however, are currently unavailable. Thus, it would be desirable to overcome these and other shortcomings of the prior art.

SUMMARY OF THE INVENTION

The present teachings are generally related to patella tracking components, as well as methods for using such components to track a patella during a surgical navigation procedure.

According to one aspect of the present teachings, an apparatus for use in tracking movement of a patella through a range of motion during a surgical navigation procedure, comprises a frame fixed in relation to the patella, a patella trial component associated with the frame for fixing the frame relative to the patella, and a reference array configured to attach to the frame, the reference array having first, second and third markers, the first, second and third markers being detectable by a surgical navigation system when exposed to a measurement field of the surgical navigation system.

In accordance with another aspect of the present teachings, a method for tracking a patella with a surgical navigation system is provided. The method comprises providing a tracking system and a surgical component that is detectable by the tracking system, touching a portion of the surgical component against a surface of the patella, moving a leg attached to the patella through a range of motion as the surgical component is maintained against the surface of the patella, and using the tracking system to determine a path the patella travels as the leg is moved through the range of motion.

In accordance with yet another aspect of the present teachings, a surgical navigation system for tracking movement of a patella through a range of motion during a surgical procedure is provided. The system comprises a frame fixed in relation to the patella, a reference array configured to attach to the frame, the reference array having first, second and third markers, the first, second and third markers being detectable by a surgical navigation system when exposed to a measurement field of the surgical navigation system, and a means for determining a path traveled by the patella as the patella is moved through a range of motion.

In accordance with still yet another aspect of the present teachings, an apparatus for use in tracking the movement of a patella through a range of motion during a surgical navigation procedure is provided. The apparatus comprises a frame having a movable plate that is configured to adjustably engage the patella and retain it against the frame, a pressure sensitive material associated with the frame, the pressure sensitive material being configured to detect a resistance force encountered by the patella when engaged by the plate, and a reference array configured to attach to the frame, the reference array having first, second and third markers, the first, second and third markers being detectable by a surgical navigation system when exposed to a measurement field of the surgical navigation system.

BRIEF DESCRIPTION OF DRAWINGS

The above-mentioned aspects of the present teachings and the manner of obtaining them will become more apparent and the teachings will be better understood by reference to the following description of the embodiments taken in conjunction with the accompanying drawings, wherein:

FIG. 8c is a bottom view of the patella array assembly of FIG. 8a;

FIG. 9b is a bottom view of the patella array assembly of FIG. 9a;

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Figure 1:
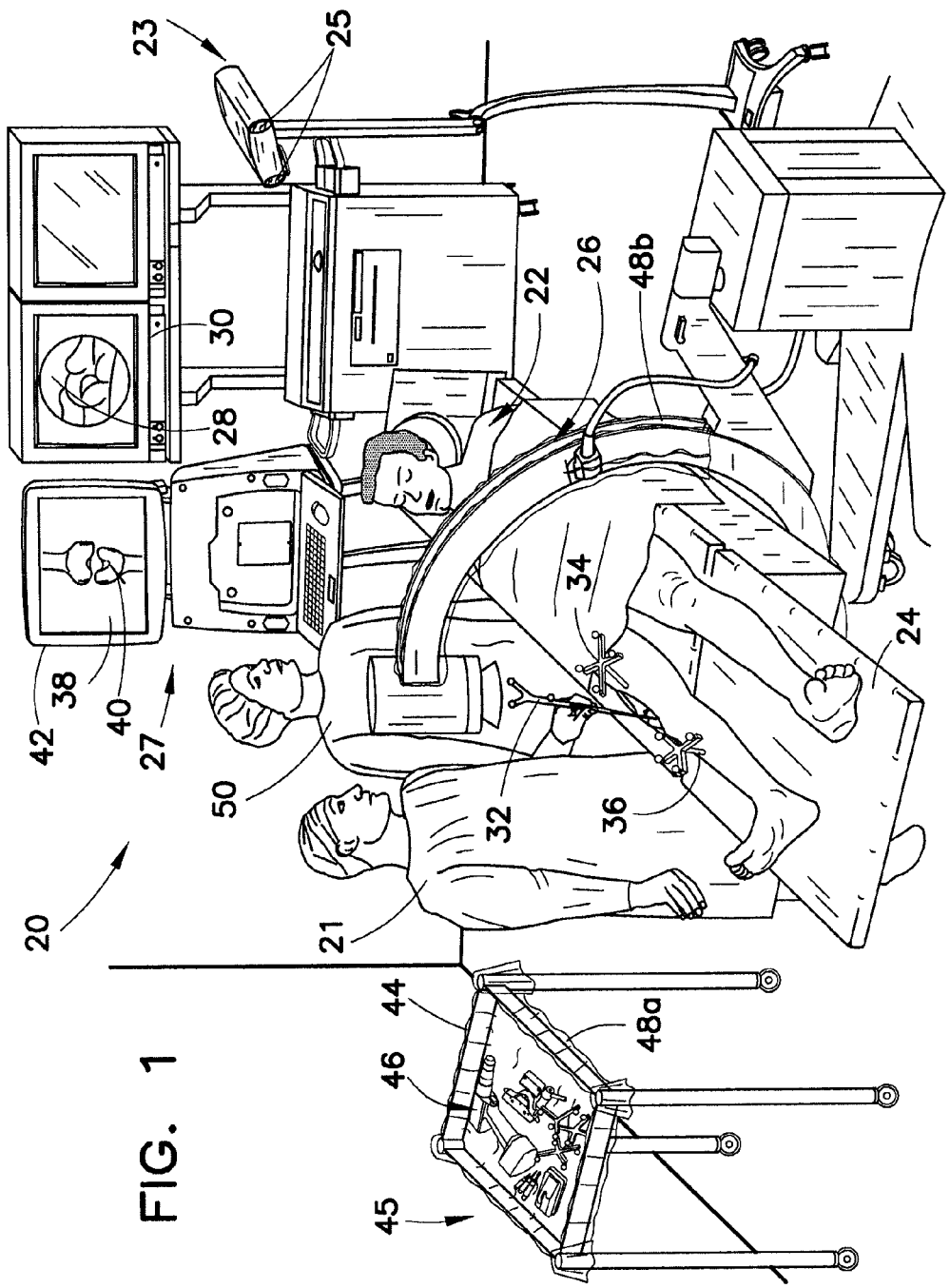
FIG. 1 is a perspective view of an operating room setup in a surgical navigation embodiment in accordance with the present teachings.

FIG. 1 shows a perspective view of an operating room with a surgical navigation system 20. A surgeon 21 is aided by the surgical navigation system in performing knee arthroplasty, also known as knee replacement surgery, on a patient 22 shown lying on the operating table 24. The surgical navigation system 20 has a tracking system that locates arrays and tracks them in real-time. To accomplish this, the surgical navigation system includes an optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The operating room includes an imaging system such as a C-arm fluoroscope 26 with a fluoroscope display image 28 to show a real-time image of the patient's knee on a monitor 30. The surgeon 21 uses a surgical probe 32 to reference a point on the patient's knee, and the reference arrays 34, 36, which are attached to the patient's femur and tibia to provide known anatomic reference points so the surgical navigation system can compensate for leg movement. The relative location of the probe array 32 to the patient's tibia is then shown as reference numeral 40 on the computer display image 38 of the computer monitor 42. The operating room also includes an instrument cart 45 having a tray 44 for holding a variety of surgical instruments and arrays 46. The instrument cart 45 and the C-arm 26 are typically draped in sterile covers 48a, 48b to eliminate contamination risks within the sterile field.

The surgery is performed within a sterile field, adhering to the principles of asepsis by all scrubbed persons in the operating room. The patient 22, the surgeon 21 and the assisting clinician 50 are prepared for the sterile field through appropriate scrubbing and clothing. The sterile field will typically extend from the operating table 24 upward in the operating room. Typically, both the computer display image 38 and the fluoroscope display image 28 are located outside of the sterile field.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with the surgical navigation system 20 or by applying a statistical anatomical model. A morphed image of the patient's anatomy can be created by combining an image of the patient's anatomy with a data set, such as a virtual image of the patient's anatomy. Some imaging systems, such as the C-arm fluoroscope 26, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3 C-Arm-Based Navigation, Springer-Verlag (2004).

The tracking system of the present teachings can be any system that can determine the three-dimensional location of devices carrying or incorporating markers that serve as tracking indicia. More particularly, the tracking system may be an active tracking system that has a collection of infrared light emitting diode (ILEDs) illuminators surrounding the position sensor lenses to flood a measurement field of view with infrared light. Alternatively, the system may be a passive tracking system, which incorporates retro-reflective markers that reflect infrared light back to the position sensor, and the system triangulates the real-time position (x, y, and z location) and orientation (rotation around x, y, and z axes). In yet other embodiments, the tracking system may be a hybrid tracking system that detects active and active wireless markers in addition to passive markers. Active marker based instruments enable automatic tool identification, program control of visible LEDs, and input via tool buttons. Finally, in yet other embodiments, the tracking system may utilize electromagnetic tracking techniques. These systems locate and track devices and produce a real-time, three-dimensional video display of the surgical procedure by using electromagnetic field transmitters that generate a local magnetic field around the patient's anatomy.

Figure 2A:
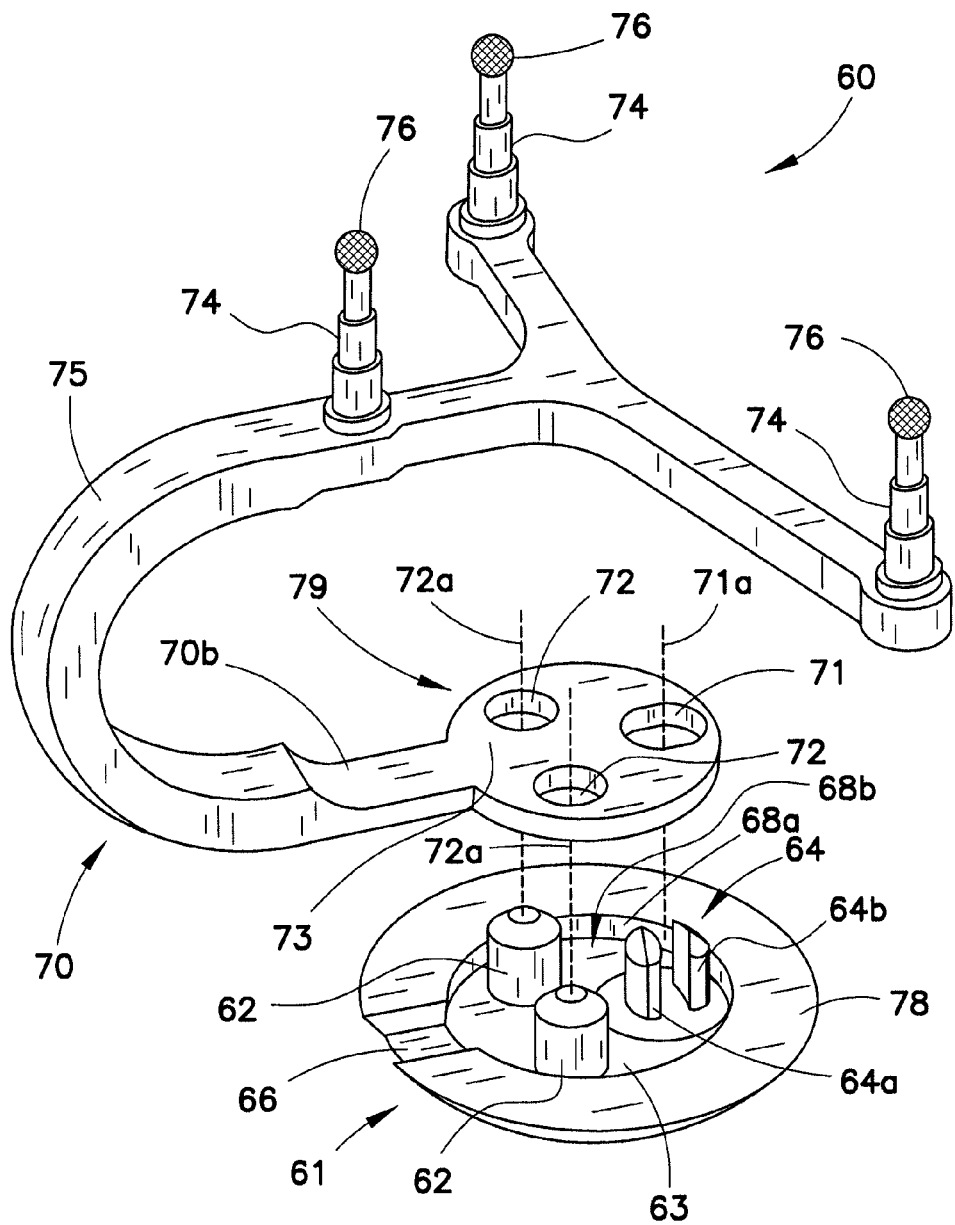
FIG. 2a is an exploded perspective view illustrating a patella array assembly in accordance with the present teachings.

The present teachings enhance the surgical navigation system 20 by incorporating into the system methods and apparatuses for tracking a patella during a surgical navigation procedure. Moving now to FIG. 2a, a first embodiment of a patella tracking apparatus in accordance with the present teachings is shown. According to this embodiment, patella array assembly 60 consists of a patella trial button/component 61 and an array component 70 having a frame 75, array towers 74 and patella receiving disk 79. In certain embodiments, the frame is substantially shaped and sized to accommodate a patella that is placed therein. For instance, in specific aspects of the present teachings, the frame is C-shaped thereby creating a clip-like structure, which is designed to accommodate the patella during a surgical procedure.

The patella trial button 61 has one or more studs or prongs (e.g., rounded studs 62 and slotted stud 64), which extend upwardly from a bottom surface 63 of the button. While not required, in certain embodiments the studs 62 and 64 can be substantially the same height. As will be explained below, the studs 62 and 64 are configured to interface with holes that are drilled into a patella during a surgical procedure. The slotted stud 64 includes two halves (64a and 64b), both of which bias slightly outwardly so that when the stud is inserted into the drilled patella hole, the halves 64a and 64b press against the inner surface of the hole to create a secure fit. While this embodiment shows a configuration having three studs, it should be appreciated that other configurations may also be used as desired without straying from the present teachings. As such, the present teachings are not intended to be limited herein.

Figure 2B:
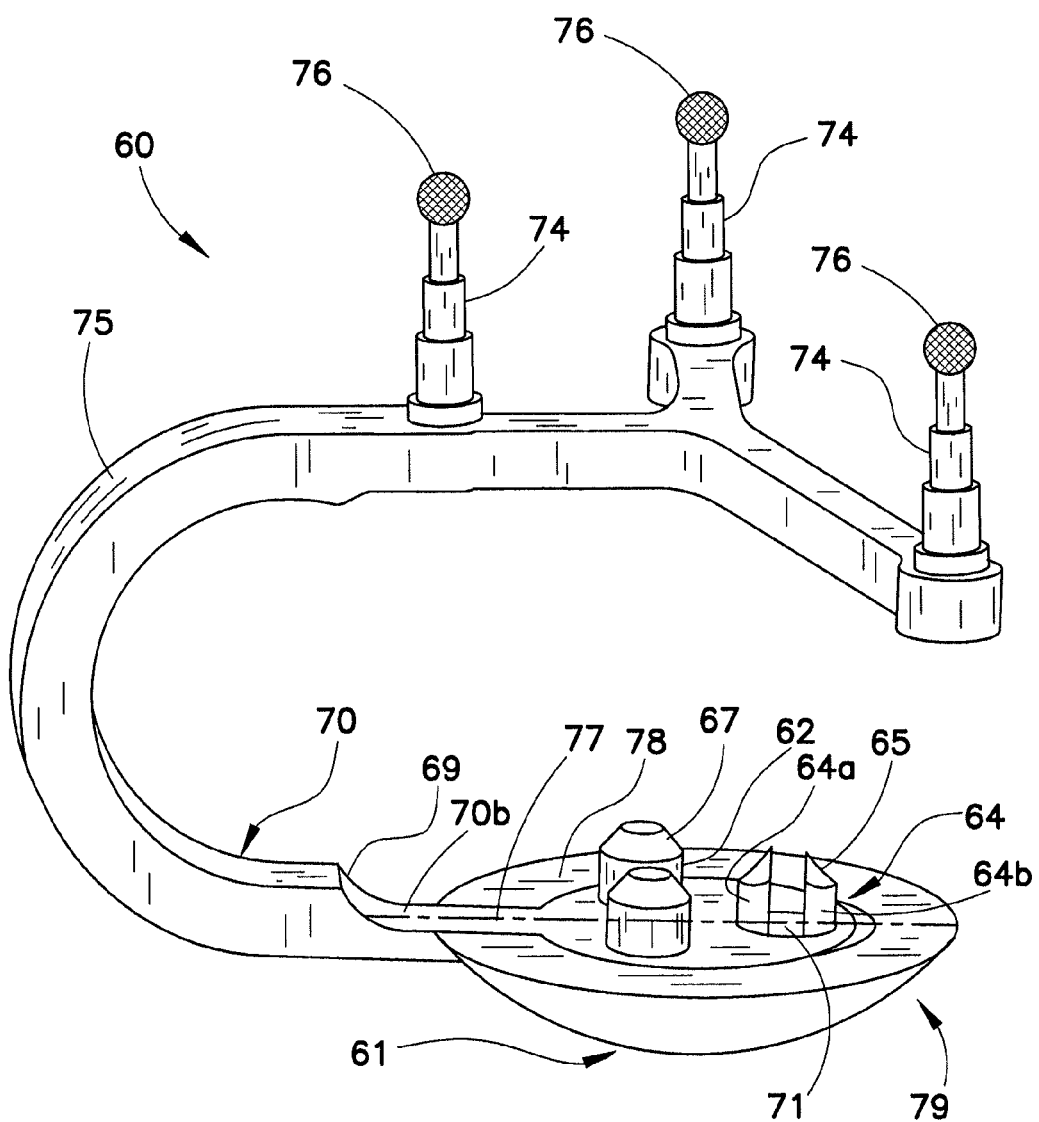
FIG. 2b is a perspective view of the patella array assembly of FIG. 2a shown assembled.

In addition to the bottom surface 63, the patella trial button 61 also has a flanged top surface 78 and a sidewall 68a, which together define a recessed cavity 68b for receiving the patella receiving disk 79 during assembly. More particularly, during assembly, the patella receiving disk 79 is placed inside the recessed cavity 68b such that top surfaces 73 and 78 align to create a substantially flat resting surface 77, as shown in FIG. 2b, which is adapted to support the patella during the surgical procedure. To achieve this aligned orientation, a portion 66 of the trial button's flanged top surface 78 is removed to receive a portion 70b of the array assembly's frame 75.

The array towers 74 of the array component 70 are spaced apart by the frame 75 so that the array markers 76 can be independently recognized and tracked by the CCD cameras 25 of the optical locator 23 during a surgical procedure. The array component 70 also has a series of holes (e.g., round holes 72 and oval hole 71), which are used to assemble the patella array assembly 60. More particularly, during assembly, the rounded studs 62 are advanced through the round holes 72 along line 72a, while the slotted stud 64 is advanced through the oval hole 71 along line 71a. It should be understood and appreciated herein that the diameter of the studs is slightly less than that of the holes so that the studs are able to fit through the holes and achieve a friction fit thereto.

Turning now to FIG. 2b, once the patella array assembly 60 is assembled, a portion of the slotted stud 64 protrudes out of the oval hole 71 of the array component 70 and biases slightly outwardly as described above. Moreover, the studs 62 and 64 have chamfered edges 67 and 65, respectively, which facilitate the array assembly 60 to be guided into pre-drilled holes of the patella as the trial button 61 is attached to the patella. The transition from a flat surface to an inflection point 69 creates the resting surface 77 for the patella, as well as serves to stabilize the patella as the surgeon manipulates the patella during the surgical procedure.

Figure 3:
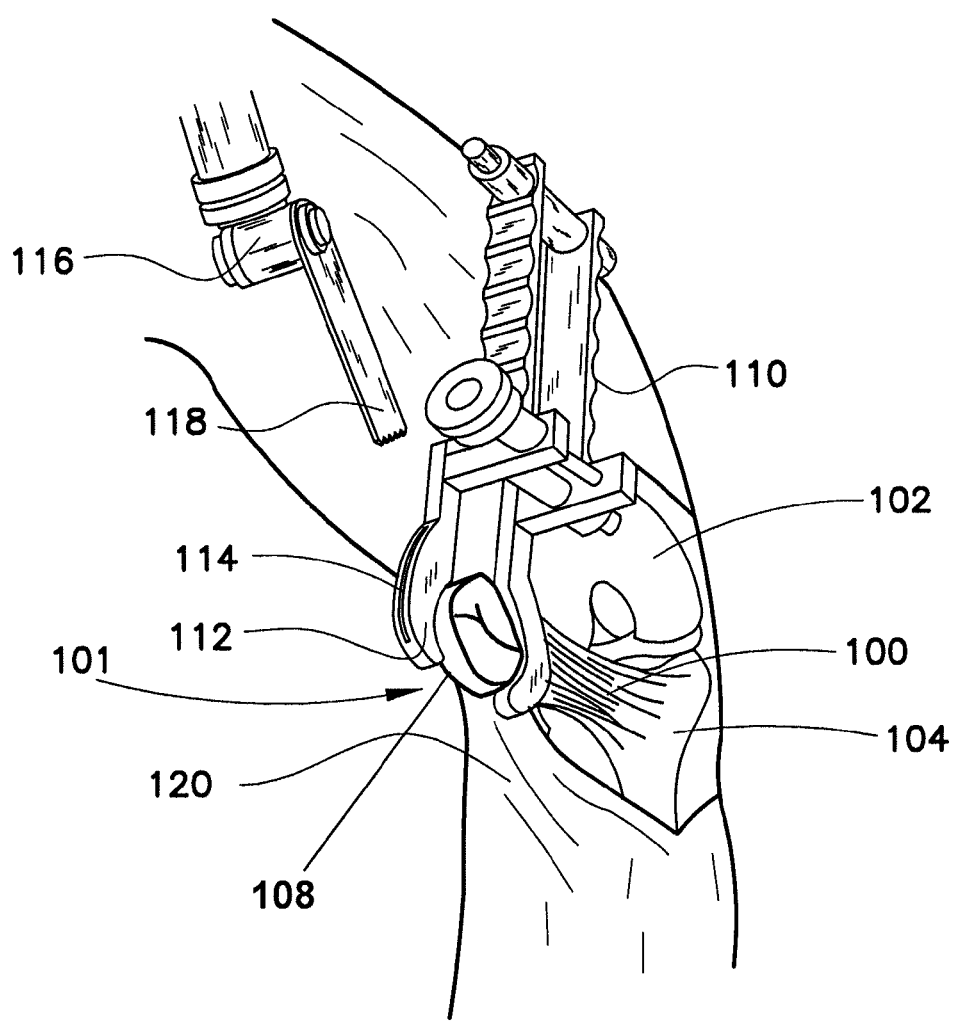
FIG. 3 is a fragmentary perspective view illustrating a patella resurfacing procedure.

The principles upon which various embodiments of the present teachings rely can be further understood with reference to FIG. 3, which illustrates a surgeon preparing to resurface a patient's patella prior to attaching a trial button, More particularly, after an incision has been made to the patient's leg 120, the surgeon exposes the knee cavity 101 to access the patient's femur 102, tibia 104, patella 108 and patella tendons 100. Once the knee cavity 101 is opened and accessible to the surgeon, the patella 108 is grasped with the clamping jaws 112 of a clamping device 110 and its position manipulated so that the side of the patella to be resurfaced is readily accessible to the surgeon for resection. Once the patella 108 is securely held by the clamping jaws 112 and positioned appropriately for the resection process, the surgeon places a cutting blade 118 of a cutting tool 116 through a cutting guide 114 associated with the clamping jaws 112 and resects the surface of the patella 108 that is natively in contact with the femur 102 and the tibia 104. It should be noted that in other embodiments the surgeon could alternatively cut or resect the patella surface directly and without the use of a cutting guide. As such, the present teachings are not intended to be limited.

Figure 4:
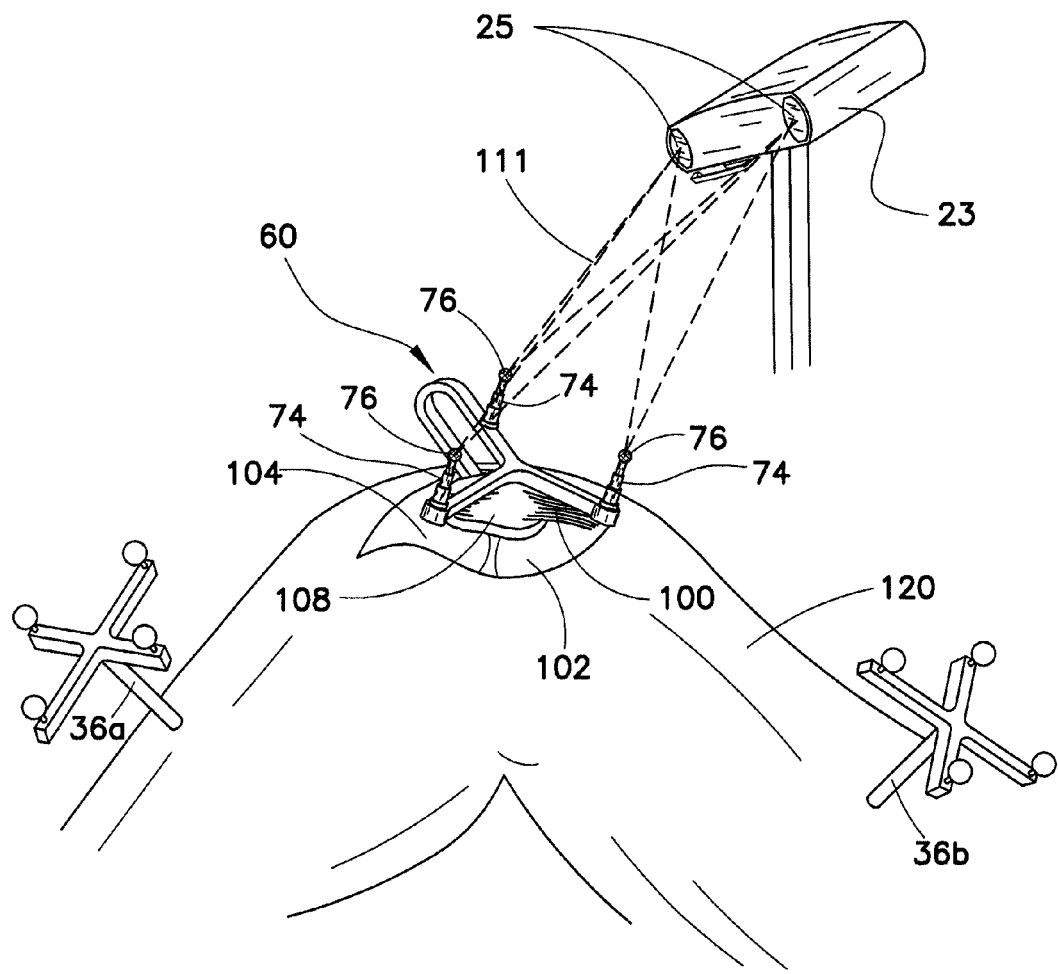
FIG. 4 is a fragmentary perspective view illustrating a patella tracking procedure in accordance with the present teachings.

After the patella has been resurfaced, a drill guide template (not shown) is placed over the resurfaced patella and is used for drilling holes into the surface of the patella 108. According to certain embodiments of the present teachings, the spatial orientation of the holes on the drill guide template are arranged such that they substantially correspond with or match the orientation of the studs 62 and 64 on the trial button 61. As shown in FIG. 4, after the holes are drilled into the patella, the trial button is secured to the patella 108 so that its relative position can be tracked by the navigation system. With respect to the manner by which the assembly is secured to the patella, such assembly should be secured so that the array markers 76 have a clear optical path to the optical locator 23 and its CCD cameras 25. By having a clear optical path, as the surgeon moves the patella array assembly 60 relative to the patient's femur 102 and tibia 104, the tracking system locates and tracks the patella array assembly in real-time (see the optical path/measurement field of the tracking system represented by dashed lines 111). To accomplish this, the cameras 25 of the optical locator 23 detect the position of the patella array assembly 60 in space by using triangulation methods, which reference the position of the array assembly as it moves with respect to the rigid reference arrays 36a and 36b, which are fixably attached to the tibia and femur of the patient, respectively. The relative location of the patella array assembly 60 with respect to the patient's leg 120 may then be shown as a real-time image on a computer display during the surgical procedure.

To track the position of the patella 108 with respect to the femur 102 and the tibia 104, the surgeon 21 must next register the patella 108 with the navigation system 20 by collecting various points or bony landmarks on the patella 108. More particularly, in accordance with certain aspects of the present teachings, the surgeon intra-operatively acquires individual surface landmarks of the patient's anatomy with a surgical probe (or other similar instrument) as the probe is detected and tracked by the navigation system. By acquiring these landmarks and registering them with the navigation system's computer, a surgeon can accurately navigate a biomedical implant to an intra-operatively planned position, as well as gather important surgical information, such as gap analysis data, resection plane details and bone and/or surgical component alignment angles.

As is appreciated by those within the art, bony landmarks are visible points or locations on a patient's anatomy, which are identifiable by referencing known locations on the surface of the bone. For instance, known bony landmarks on the femur include, but are not limited to, the medial and lateral condyles, the medial and lateral epicondyles, the medial and lateral posterior condyles, and the anterior cortex. Similar bony landmarks are also found on other bones, such as the tibia, fibula, patella and pelvis, for instance.

After the patella 108 has been registered, the surgeon 21 then tracks the patella trial button 61 as it articulates or moves with respect to the femur and tibia by tracking the relative movement of the array assembly 60. At this point in the procedure, it should be understood that trial components are attached to the patient's bones, particularly as these trial components can be independently moved, manipulated and/or fine adjusted as needed before the final implants are secured to the patient's anatomy. To this end, it should also be understood and appreciated herein that upon removal of the patella trial button/component 61 from the patella, the permanent patella implant can be fitted to the patella using the same holes and engagement location as was used by the trial component. Since the same series of patella holes are used for both the trial and permanent patella components, the surgical procedure can be performed less invasively, thereby improving the recovery time of the patient undergoing the operative procedure.

Figure 5:
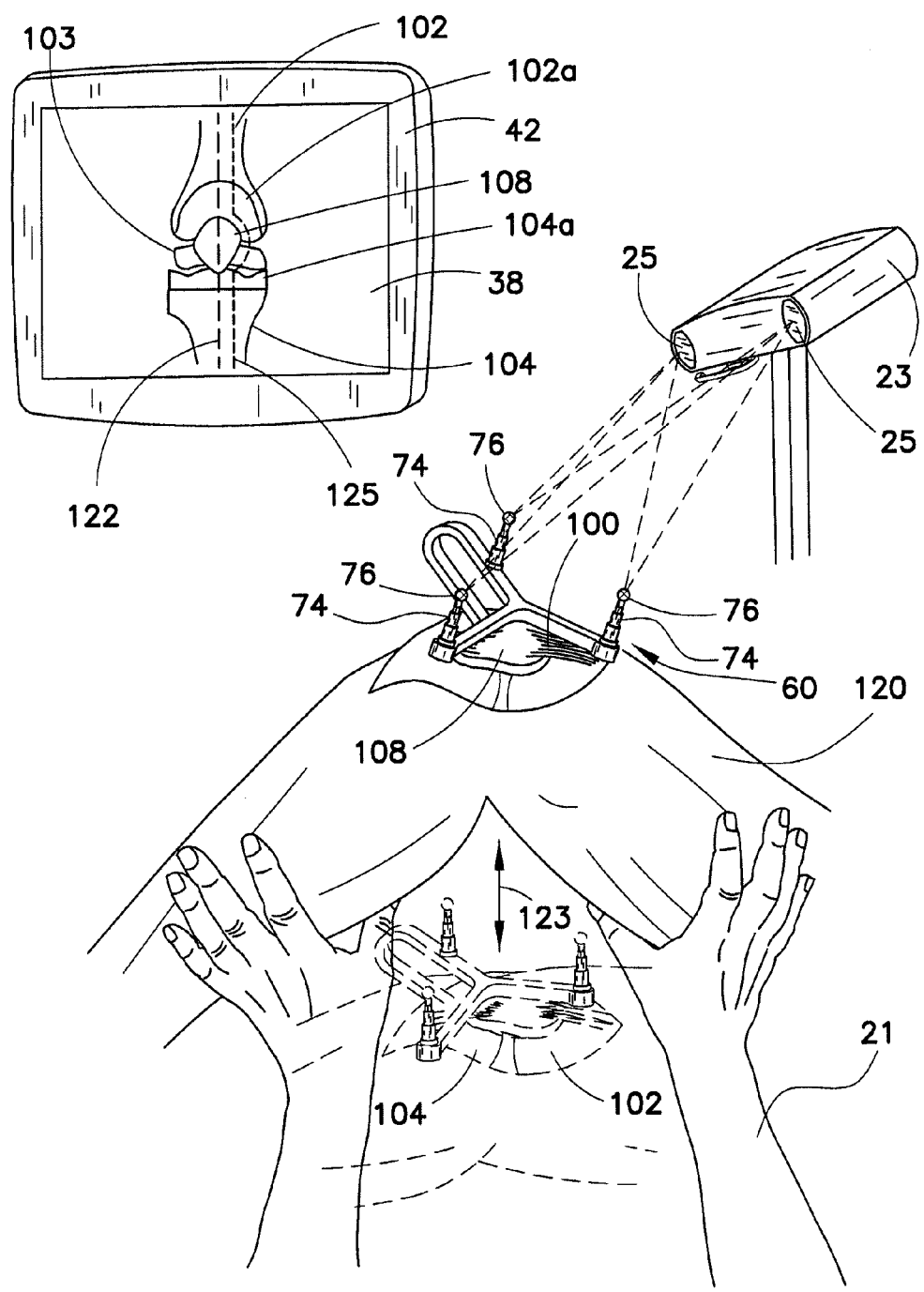
FIG. 5 is a fragmentary perspective view illustrating a patella array assembly being tracked as a leg is moved through a range of motion between flexion and extension during a surgical procedure in accordance with the present teachings.

Moving now to FIG. 5, a patella array assembly 60 being tracked in accordance with the present teachings is depicted. In this illustration, the surgeon 21 manipulates the patient's leg 120 from a flexion position to an extension position (as indicated by solid and phantom lines), while the patella 108 is engaged by the patella array assembly 60. In this illustration, the surgeon moves the leg in the direction indicated by arrow 123 between the flexion and extension positions to determine if the leg is properly traveling along a desired axial path as defined by the leg's mechanical axes. If the leg is not traveling this intended path, then the natural joint function of the leg will not be achieved and the life of the implanted components could be lessened or negatively impacted. More particularly, as is known in the art, before implanting knee prosthetic components, the mechanical axis of the femur (which connects the center of a patient's hip with the center of the patient's knee) and the mechanical axis of the tibia (which connects the center of the patient's knee with the center of the patient's ankle) should be determined. These axes are determined because the resections performed prior to installing the femoral and tibial components must be aligned in accordance with these respective axes. The exact positions of the resection surfaces on the femur and tibia are crucial if the knee prosthetics are to have long working lives. As such, the surgeon must establish the standard bearing surfaces of the resection planes on the femur and tibia according to geometrical specifications of the knee prosthetics while taking into account their respective mechanical axes. In some cases, pathological displacements must also be corrected and allowances must be made for the position and action of the ligaments and muscles that are present in the leg. To confirm the leg is indeed traveling the correct and intended femoral-tibial mechanical axis, the surgeon tracks the leg as it is moved through a range of motion. This tracked movement tells the surgeon if the position of one or more of the surgical components should be adjusted, particularly if the leg is not traveling its intended path when moved through flexion and extension.

To determine the femoral and tibial mechanical axes, the surgeon touches a surgical probe against the surface of the femur and tibia at two individual locations that together form a line defining the respective femoral and tibial mechanical axes. As is explained above, such surgical probes include markers, which are identified and tracked by cameras of an optical locator. As the surgeon positions the surgical probe at the individual locations on the femur and tibia, the tracking system locates and tracks the markers in real-time and detects their positions in space by using triangulation methods. The relative locations on the femur and tibia are then shown on a surgical plan image. To accomplish this, the tracking system detects the location of the surgical probe as it is positioned relative to the femur and the tibia by referencing the position of the markers as they move with respect to reference arrays (e.g., 36a, 36b), which are fixably attached to the tibia and femur. After the individual locations on the tibia and femur are acquired by the surgical probe, a representation of the femoral-tibial mechanical axis is then generated and shown on the surgical plan image for use by the surgeon.

To better understand and appreciate the present teachings, an illustration of a leg being moved through a range of motion to determine if it aligns with the femoral-tibial mechanical axis is now provided. With reference to FIG. 5, as the leg 120 is moved substantially along line 123, the relative position of the array markers 76 on the patella array assembly 60 is detected and tracked in real-time by the CCD cameras 25 of the optical locator 23. The surgeon 21 observes this movement on a computer monitor 42, which displays a computer image 38 of the leg, including the femur 102, the tibia 104 and the patella 108, as well as the femoral component 102a, the tibial component 104a and a polyethylene component 103. The femoral-tibial mechanical axis 122 is also shown on the computer image, which illustrates the path the leg is intended to travel when articulated from flexion to extension. As can be seen in this illustrative embodiment, when the surgeon moves the leg between flexion and extension, the leg is not traveling along this intended path, but instead is traveling along a slightly different path, which is shown here as dashed line 125. This flawed leg movement informs the surgeon that the implanted components (i.e., the patella trial button/component 61, the femoral component 102a, the tibial component 104a and the polyethylene component 103) may not be properly aligned, angled and/or sized with respect to one another. Such misalignment can be problematic, particularly as it is generally understood that misaligned components can cause premature failure of the implants, as well as chronic postoperative pain and discomfort for the patient. If the surgeon determines that the leg is not traveling along its intended femoral-tibial mechanical axis during flexion/extension, the surgeon can correct this misalignment by adjusting the lateral, medial and/or angular position of one or more of the temporarily placed trial surgical components.

Figure 6:
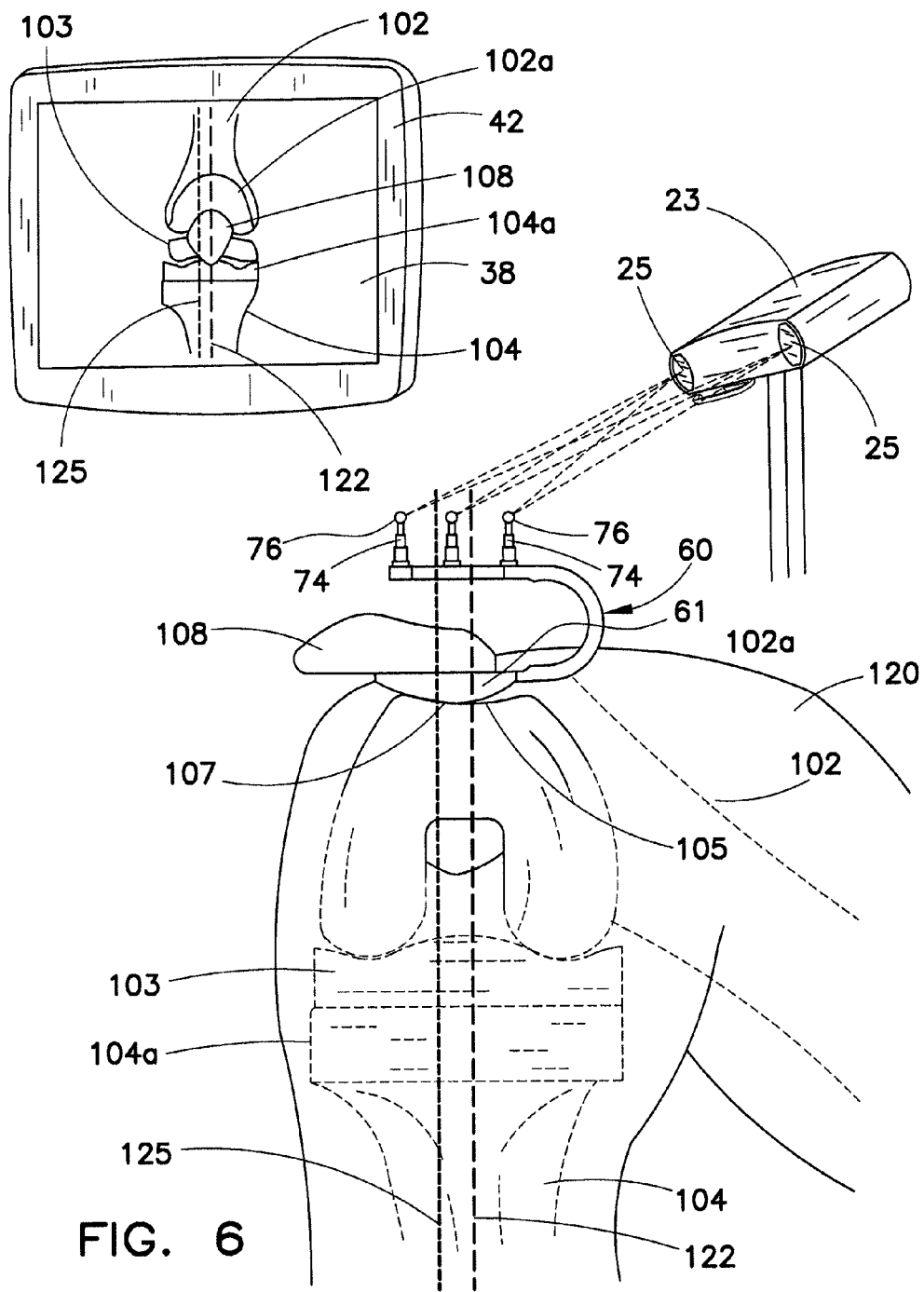
FIG. 6 is a fragmentary perspective view illustrating a patella array assembly being aligned relative to an implanted femoral component in accordance with a patella tracking procedure of the present teachings.

The misalignment of FIG. 5 is further shown with reference to FIG. 6, which illustrates the patient's leg in a flexion position. More particularly, as explained above, when the surgeon moves the leg between flexion and extension, the leg is not traveling along the femoral-tibial mechanical axis 122, but instead is traveling along a slightly different path 125 or axis. As such, the implanted components may not be properly aligned, angled and/or sized with respect to one another. According to this illustration, a bottom portion 107 of the patella trial button 61, which is attached to the resurfaced portion of the patella 108, is slightly offset or misaligned from a corresponding top portion 105 of the femoral component 102a to which it is supposed to align. This slight offset between the prosthetic components causes the leg 120 to travel about an axial path 125 that is slightly off center from the intended femoral-tibial mechanical axis 122 while the leg is moved from flexion to extension. As the leg is not properly traveling along the femoral-tibial mechanical axis 122, the surgeon knows that the lateral, medial and/or angular position of the temporarily placed trial surgical components is misaligned thereby causing flawed movement of the leg through extension. The surgeon can correct this misalignment by adjusting the positioning and/or sizing of one or more of the surgical components, such as the femoral component, which is configured to articulate against the surface of the patella trial button 61 during movement of the leg 120. By adjusting the positioning and/or sizing of the surgical components, the surgeon is able to identify the location at which the patella implant should be installed to achieve appropriate flexion and extension of the leg through a range of motion.

Figure 7:
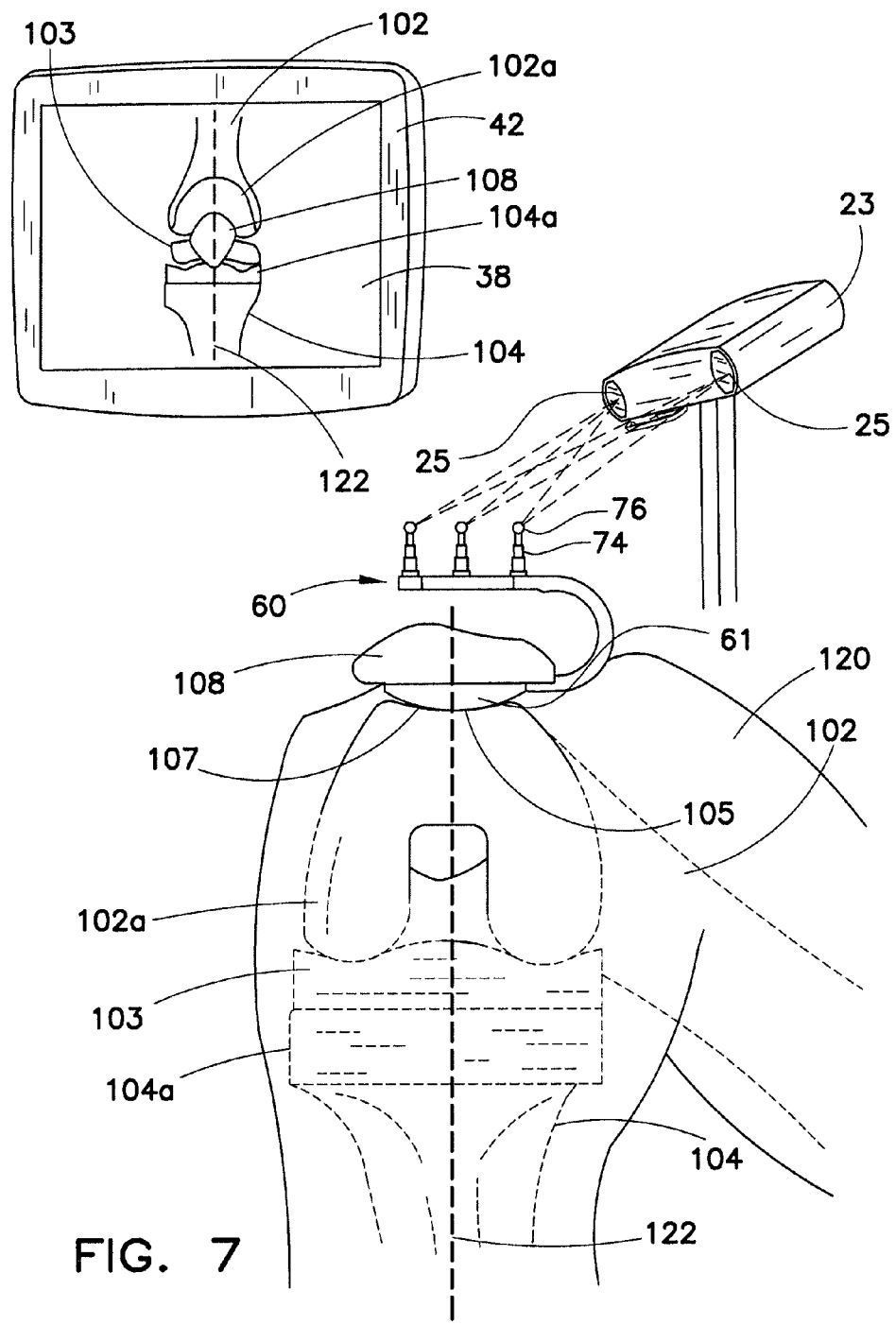
FIG. 7 is another fragmentary perspective view illustrating a patella array assembly being aligned relative to an implanted femoral component in accordance with a patella tracking procedure of the present teachings.

As is shown in FIG. 7, once the surgeon has corrected the misalignment between the bottom portion 107 of the patella trial button 61 and the top portion 105 of the femoral component, the leg 120 is once again taken through a range of motion (flexion/extension) to determine whether the leg now travels the proper femoral-tibial mechanical axis 122. According to this embodiment, and as is indicated on the computer image 38 of the display monitor 42, the leg is now substantially following the correct femoral-tibial mechanical axis 122. Thus, the surgeon can be assured the trial components are properly aligned with one another and can thereby proceed with the remaining steps of the surgical procedure.

Figure 8A:
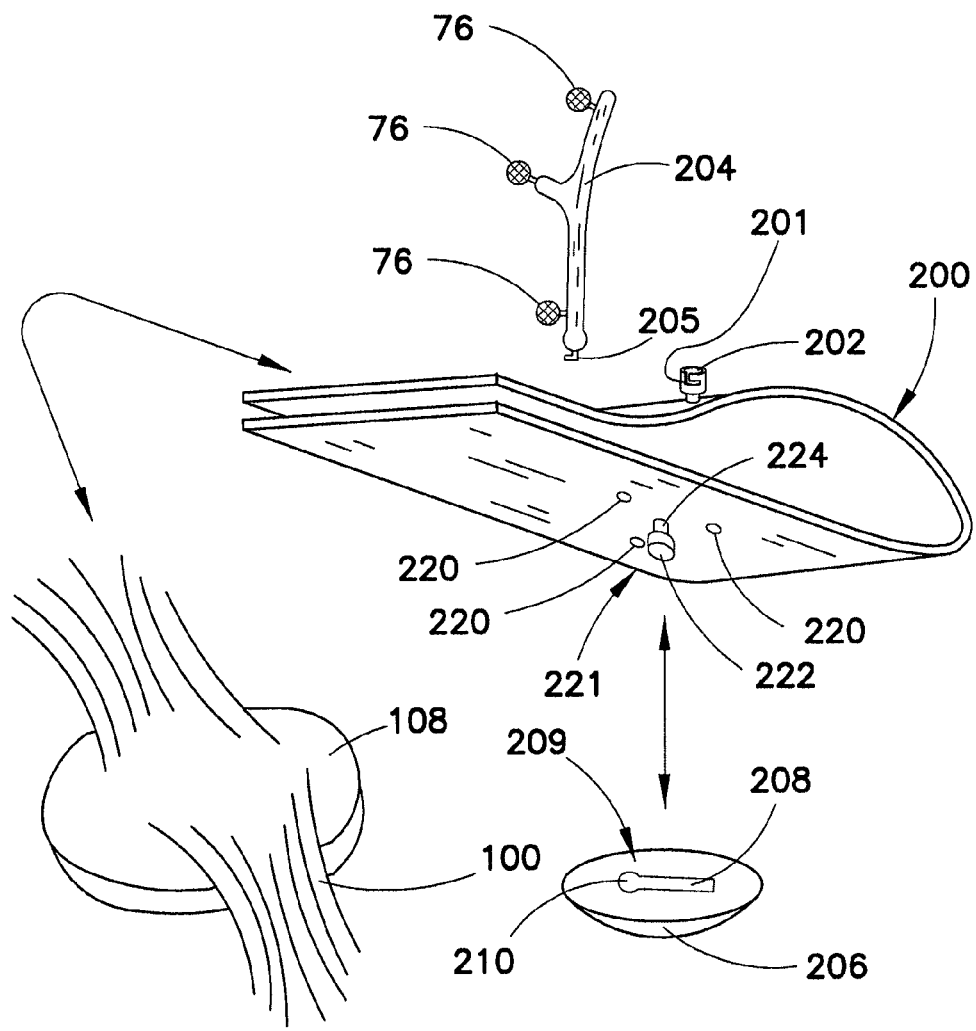
FIG. 8a is an exploded fragmentary perspective view illustrating another patella array assembly in accordance with the present teachings.
Figure 8B:
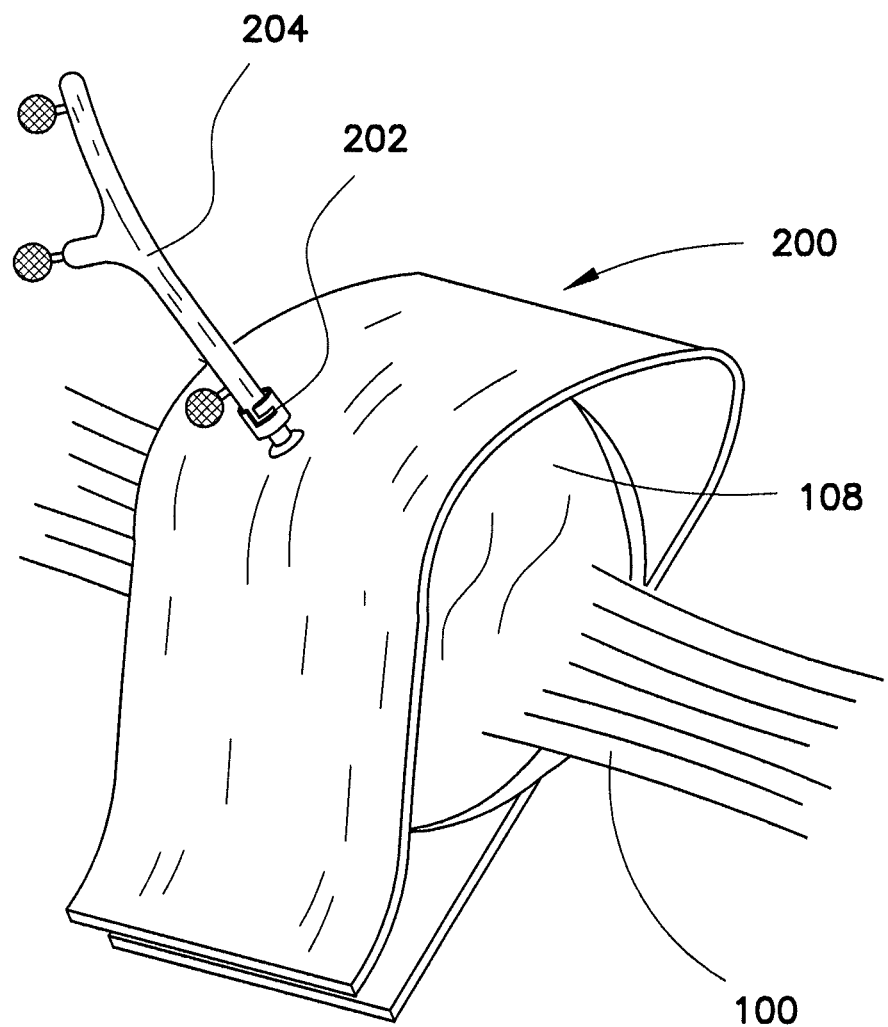
FIG. 8b is a fragmentary perspective view illustrating the patella array assembly of FIG. 8a shown engaging a patella.
Figure 8C:
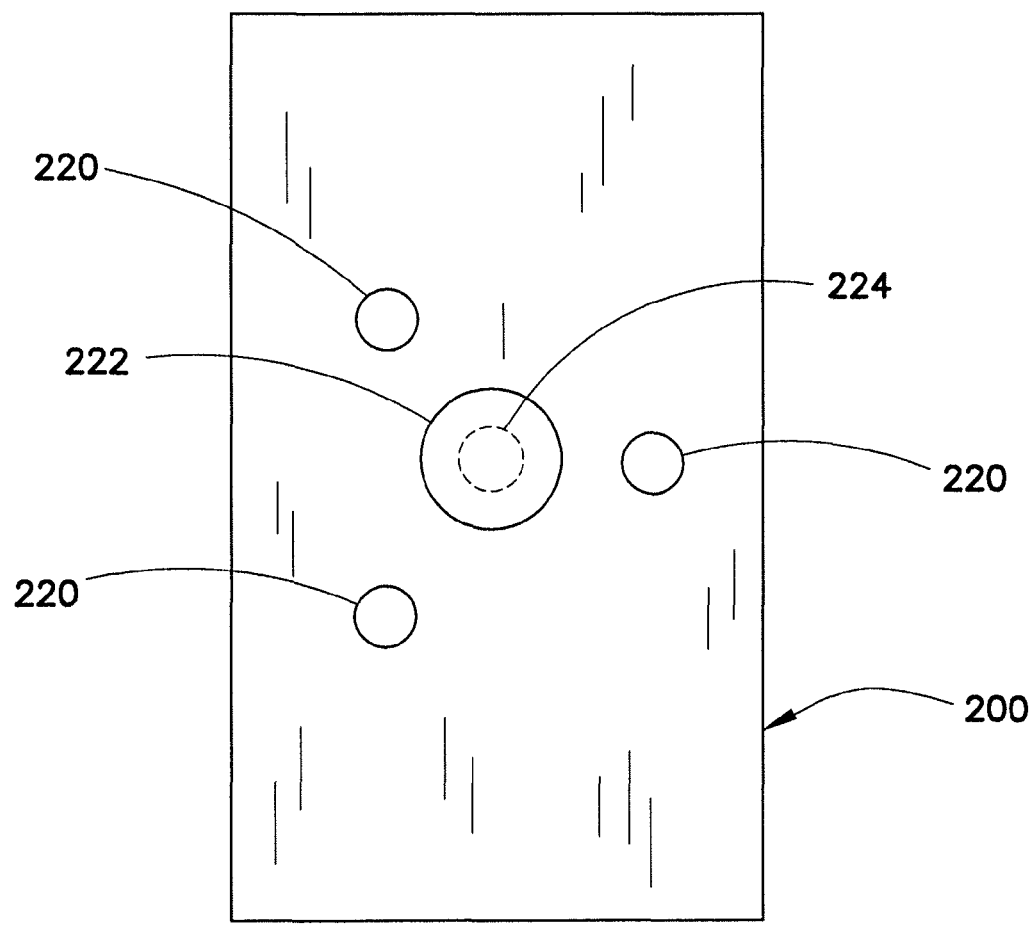

According to another embodiment of the present teachings, a spring-loaded patella clamping mechanism 200 is illustrated in FIGS. 8a-8c. On the top side of the spring-loaded clamp 200, a quick connect device 202, such as a female J-quick connect device, is provided. This quick connect device 202 is configured to interface with a removable and interchangeable array assembly 204, the array assembly being connectable to the quick connect device by sliding a pin 205 of the array assembly 204 into a corresponding groove 201 of the quick connect device 202. On the bottom side of the spring-loaded clamp 200, another quick connect device 221, such as a T-shaped quick connect, is provided, which has a post 224 having a flanged lip 222. Also shown in this embodiment is a patella trial button 206, which has a slot 209 having key openings 208 and 210. When in use, a patella 108 is slid into the spring-loaded clamp 200 while the patella tendons 100 are substantially unrestricted. Due to the compressive force of the spring-loaded clamp 200, the patella 108 is securely constrained and thereby discouraged from moving relative to the spring-loaded clamp 200. After the patella 108 is slid into the spring-loaded clamp 200 and secured into place, the clamp is connected to the patella trial button 206 by sliding the flanged lip 222 of the post 224 into key opening 210 and moving the post 224 horizontally until it enters the second narrower key opening 208. This configuration allows the patella trial button 206 to slide to a locked position, which is then centrally located on the bottom side of the spring-loaded clamp 200.

To attach the array assembly 204 to the spring-loaded clamp 200, the pin 205 of the array assembly 204 is slid into the corresponding groove 201 of the quick connect device 202 and rotated until locked into place. While this illustrative embodiment shows a quick connect attachment means being used to attach the array assembly 204 to the spring-loaded clamp 200, it should be understood that in other embodiments, the array assembly 204 may be "pre-installed" onto the spring-loaded clamp whereby no additional attachment means is required after the clamp engages the patella. It should also be understood and appreciated that any attachment means known within the art may be used to secure the array assembly 204 and/or the patella trial button 206 to the spring-loaded clamp 200. Such attachment means include, but are not limited to, welding, fusing, molding, gluing, threading, snap-connections, quick connect, quick disconnect connections and the like. For a further description about quick connect array assemblies, see U.S. patent application Ser. No. 11/299,886, entitled "IMAGE GUIDED TRACKING ARRAY AND METHOD," filed Dec. 12, 2005, which is incorporated by reference herein in its entirety.

The embodiment illustrated in FIGS. 8a-c advantageously provides drill guide holes 220 so that the surgeon 21 can drill holes into the patella 108 after the components have been appropriately aligned as desired. In other words, once the components are properly aligned and the leg extends properly through a range of motion, the surgeon can remove the patella trial button 206 and drill holes into the patella 108 through the drill guide holes 220. After the holes are drilled, the surgeon can attach a permanent patella button component to the patella and proceed with the remainder of the surgery. With respect to the resection of the patella surface in accordance with this embodiment, it should be understood and appreciated herein that the patella can be resected either before or after the spring-loaded clamp 200 is attached to the patella 108. This flexibility is possible particularly because the spring-loaded clamp can be temporarily, as opposed to permanently, attached to the patella. As such, the patella does not need to be resected or resurfaced until the prosthetic patella component is ready to be permanently attached.

For purposes of tracking a leg (and its associated components) through a range of motion, it is important to take into account the thickness of the spring-loaded clamp 200. In other words, as the spring-loaded clamp is positioned between the patella 108 and the patella trial button 206, it contributes to the distance between the patella surface and the patella trial button. When such spring-loaded clamp 200 is removed, the permanent patella trial button installed to the patella must account for this loss in thickness to thereby achieve the same tracked range of motion registered with the navigation system. One way to account for this thickness differential is to have a permanent patella button that is slightly thicker than the temporary patella button. Alternatively, the navigation system can be programmed to recognize this thickness differential and consider this information when tracking the leg through the range of motion.

FIG. 8b illustrates a patella 108 placed inside the spring-loaded clamp 200 having an array assembly 204 attached thereto. According to this illustration, the amount of force applied to the patella 108 once slid into the spring-loaded clamp is directly proportional to the resurfaced size of the patella and the equivalent spring constant of the spring-loaded clamp 200. The applied force should be large enough to appropriately secure the patella 108 in place yet not inflict damage to the patella.

FIG. 8c is a bottom view of the spring-loaded clamp 200 illustrating drill guide holes 220, as well as the post 224 and its associated flanged lip 222.

Figure 9A:
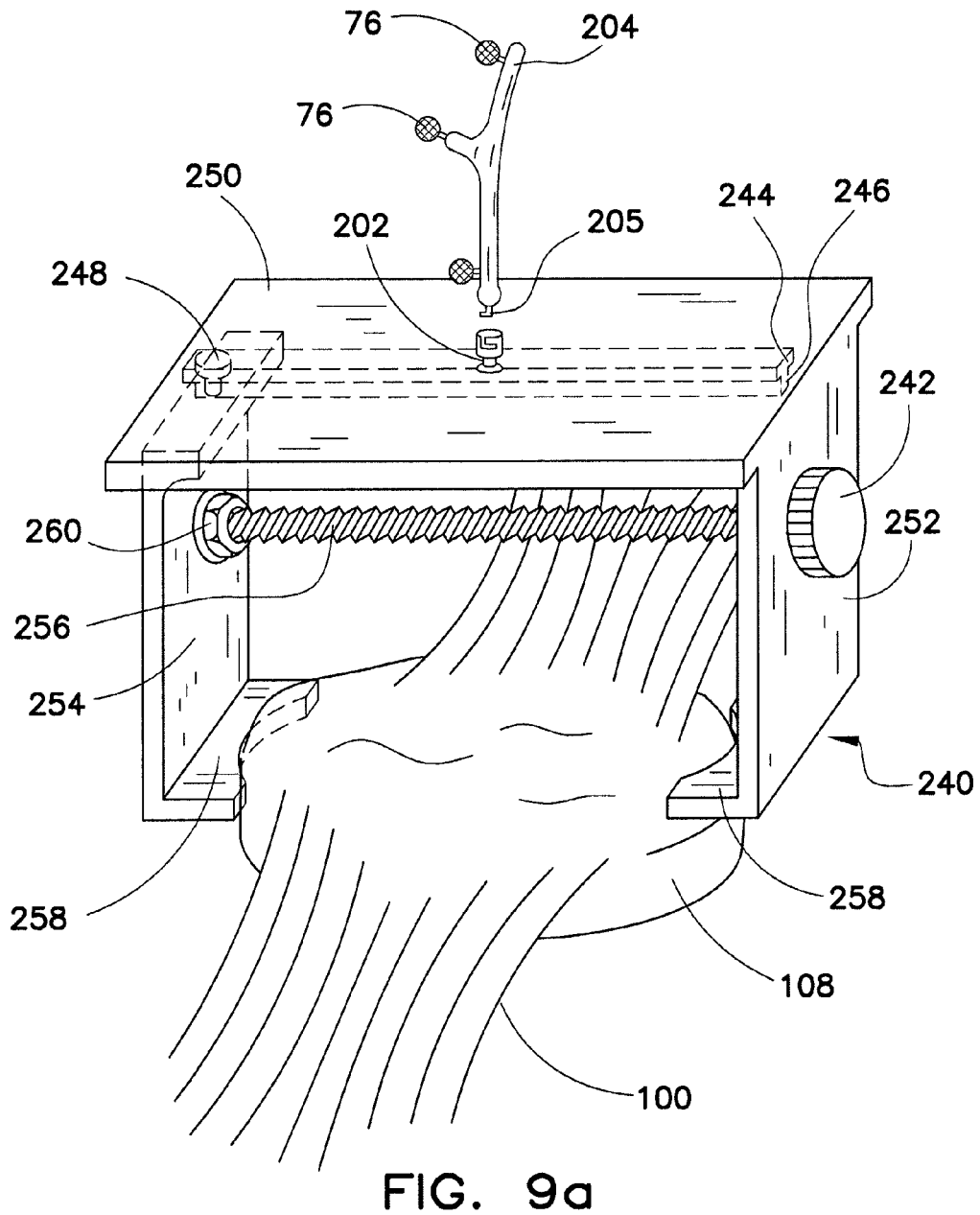
FIG. 9a is a partial fragmentary perspective view illustrating another patella array assembly engaging a patella in accordance with the present teachings.
Figure 9B:
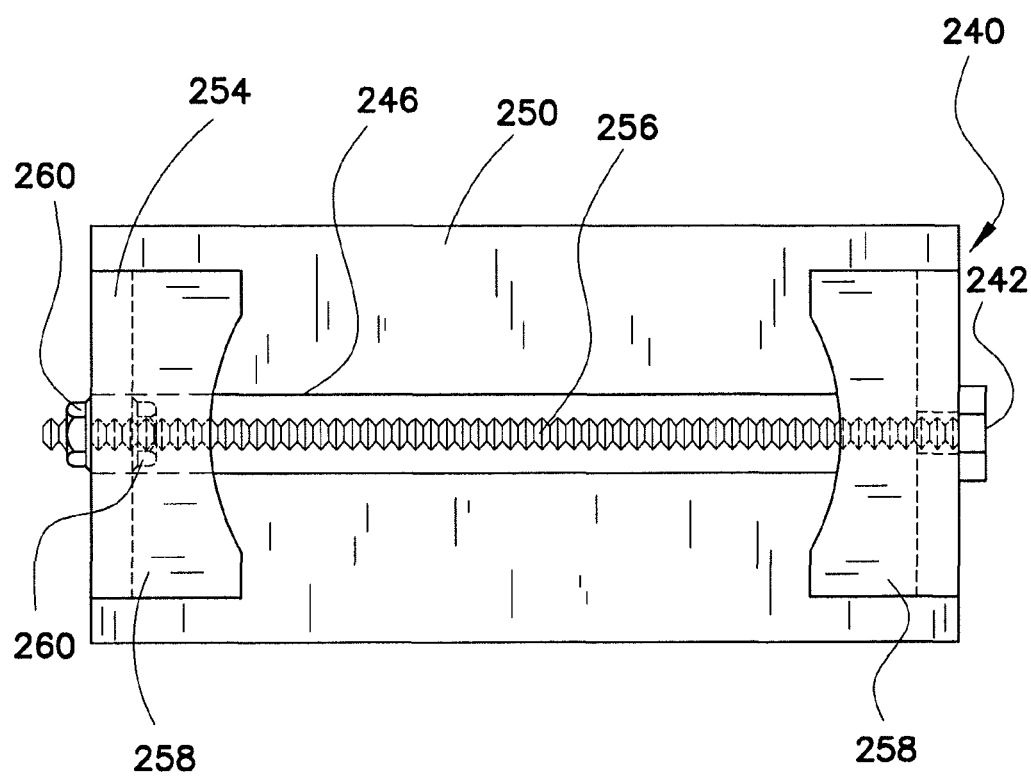

In yet another embodiment in accordance with the present teachings, a crank-type clamping mechanism is illustrated in FIGS. 9a-9b. According to this embodiment, the removable and interchangeable array assembly 204 connects to a crank-loaded clamp 240 via a channel quick connect 202. When in use, a side plate 254 of the clamp 240 moves horizontally by turning a crank 242, which causes a screw 256 to turn inside and outside of welded nuts 260, thereby forcing the side plate to move along slot tracks 244 and 246. The side plate 254 begins its movement in the slot tracks 244 and 246 by inserting the post 248 in the tracks, which on one end, reaches the edge of the top plate 250. A second side plate 252 is fixed into place such that when the turning crank 242 is actuated, the side plate 252 does not move.

The slot feature illustrated in FIG. 9a operates in a similar fashion as the slot feature in FIG. 8a. As the surgeon 21 turns the crank 242, the crank clamps 258 make contact with the patella 108 and secure it into place so that the surgeon 21 can manipulate it without relative movement between the patella 108 and the crank clamps 258. This embodiment advantageously allows the surgeon 21 to decide the amount of force that should be exerted on the patella 108 by turning the crank 242. In alternative embodiments, electronic displays, such as LEDs and LCDs may be mountable to the crank-loaded clamp 240 to display the amount of force the surgeon 21 exerts on the patella 108. According to these alternative embodiments, the surgeon 21 may use this feedback information along with bone density information to determine the appropriate amount of force needed to secure to the patella without causing damage. Moreover, in certain embodiments, the crank-loaded clamp may be equipped with a pressure sensitive material or film, such as FlexiForce® Load/Force Sensors and System manufactured by Tekscan Incorporated, 307 West First Street, South Boston, Mass. 02127-1309. This film allows the pressure encountered by the crank clamps 258, when they respectively contact the patella 108 during the engagement process, to be determined. More particularly, when either one of the crank clamps 258 encounter the patella 108, that clamp will meet a resistance force to sideways movement. Because one or more of the crank clamps 258 contain a pressure sensitive material, the resistance can be detected by a transmitter device and translated into a pressure reading to be transmitted to the computer system via a communication link. In one embodiment according to the present teachings, the transmitter may be an infrared transmitter device capable of establishing a communication link with the navigation system. Infrared transmission devices are known in the art and do not need to be discussed in further detail here.

FIG. 9b is a bottom view of the clamping mechanism 240. In this view, the side plate is shown fastened to the screw 256 by a welded locking nut 260. However, it should be understood and appreciated herein that other fastening techniques known to those of skilled in the art may also be used to fasten the side plate 254 to the screw 256. It should also be understood and appreciated herein that while FIGS. 9a and 9b do not show an illustration of a patella trial button (e.g., patella trial button 61, for instance) attached to the patella 108, such a patella trial button can be used in conjunction with this illustrative embodiment, particularly to assist with holding the crank-loaded clamp 240 in engagement with the patella 108. As such, the present teachings are not intended to be limited herein.

Figure 10:
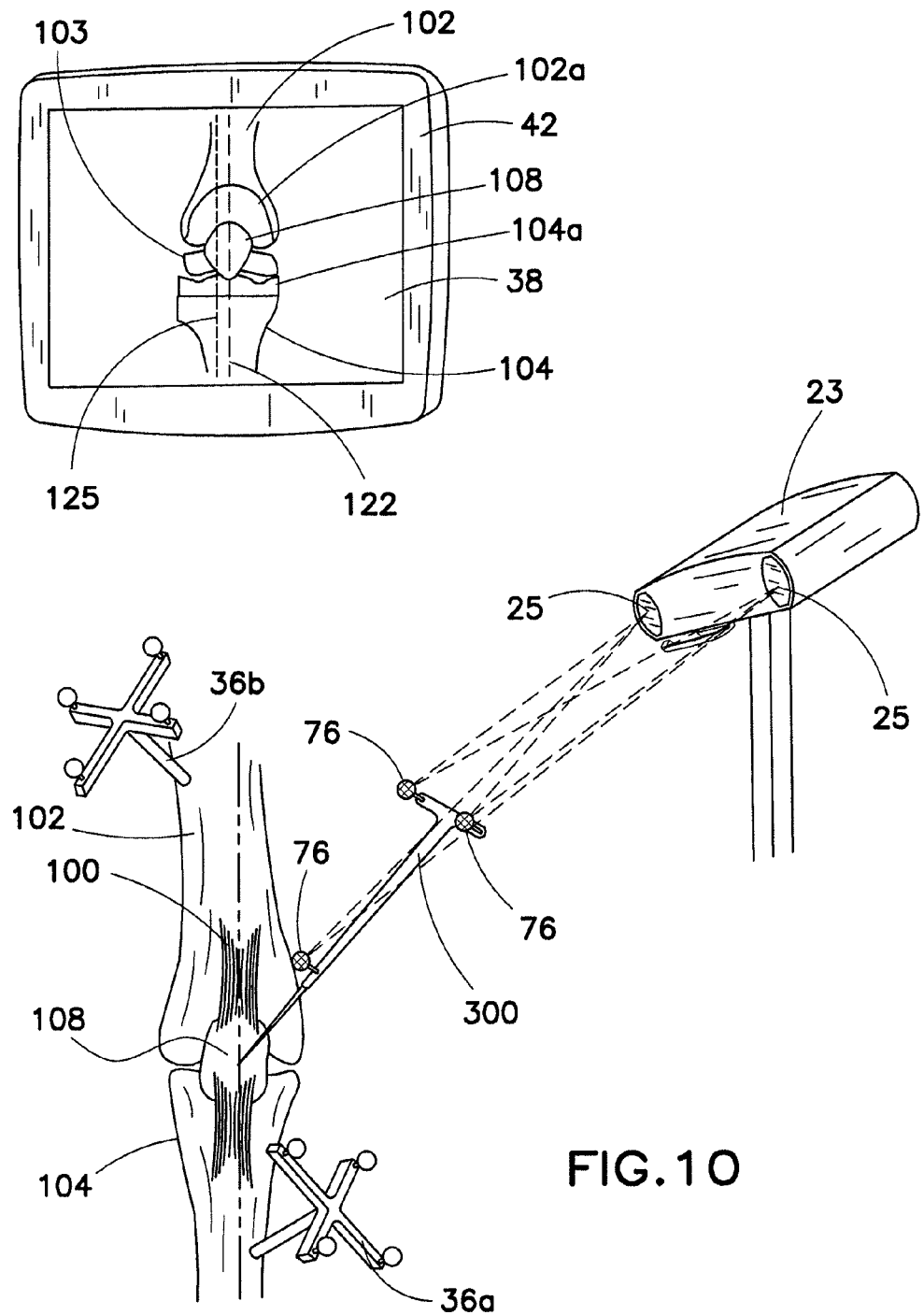
FIG. 10 is a partial fragmentary perspective view illustrating another patella tracking procedure in accordance with the present teachings.

Moving now to FIG. 10, another embodiment in accordance with the present teachings is illustrated. According to this embodiment, a surgeon uses a hand-held probe array 300 to locate the femoral-tibial mechanical axis 122. More particularly, the surgeon determines the femoral-tibial mechanical axis 122 by touching/acquiring the surgical probe array 300 against the surface of the femur and tibia at two individual locations that together form a line defining the respective femoral and tibial mechanical axes. The surgical probe array 300 includes markers 76, which are identified and tracked by cameras 25 of the optical locator 23. As the surgeon positions the surgical probe array 300 against the femur 102 and tibia 104, the tracking system locates and tracks the markers 76 in real-time and detects their position in space by using triangulation methods. To accomplish this, the tracking system detects the location of the surgical probe array 300 as it is positioned relative to the femur 102 and the tibia 104 by referencing the position of the markers 76 as they move with respect to the reference arrays 36b and 36a, which are fixably attached to the femur and tibia, respectively. After the femoral-tibial mechanical axis 122 is acquired by the surgical probe array 300, a representation is then shown as a computer display image 38 on the computer monitor 42 for use by the surgeon during the surgical procedure.

After the femoral-tibial mechanical axis 122 is determined, the surgeon can hold the tip of the probe array 300 against the patella 108 at a center point and move the leg through a range of motion between flexion and extension to evaluate movement of the leg with respect to the femoral-tibial mechanical axis 122. In other words, as the surgeon moves the leg between flexion and extension, the computer display image 38 on the computer monitor 42 displays the actual axial path 125 the leg is moving with respect to the femoral-tibial axis 122. Based on the relative positions of these two axes (i.e., 122, 125), the surgeon 21 can decide whether further alignment is needed. For instance, the surgeon can correct a misalignment by adjusting the positioning of one or more of the surgical components, such as the femoral component, which is configured to articulate against the surface of the patella trial button during movement of the leg.

Figure 11:
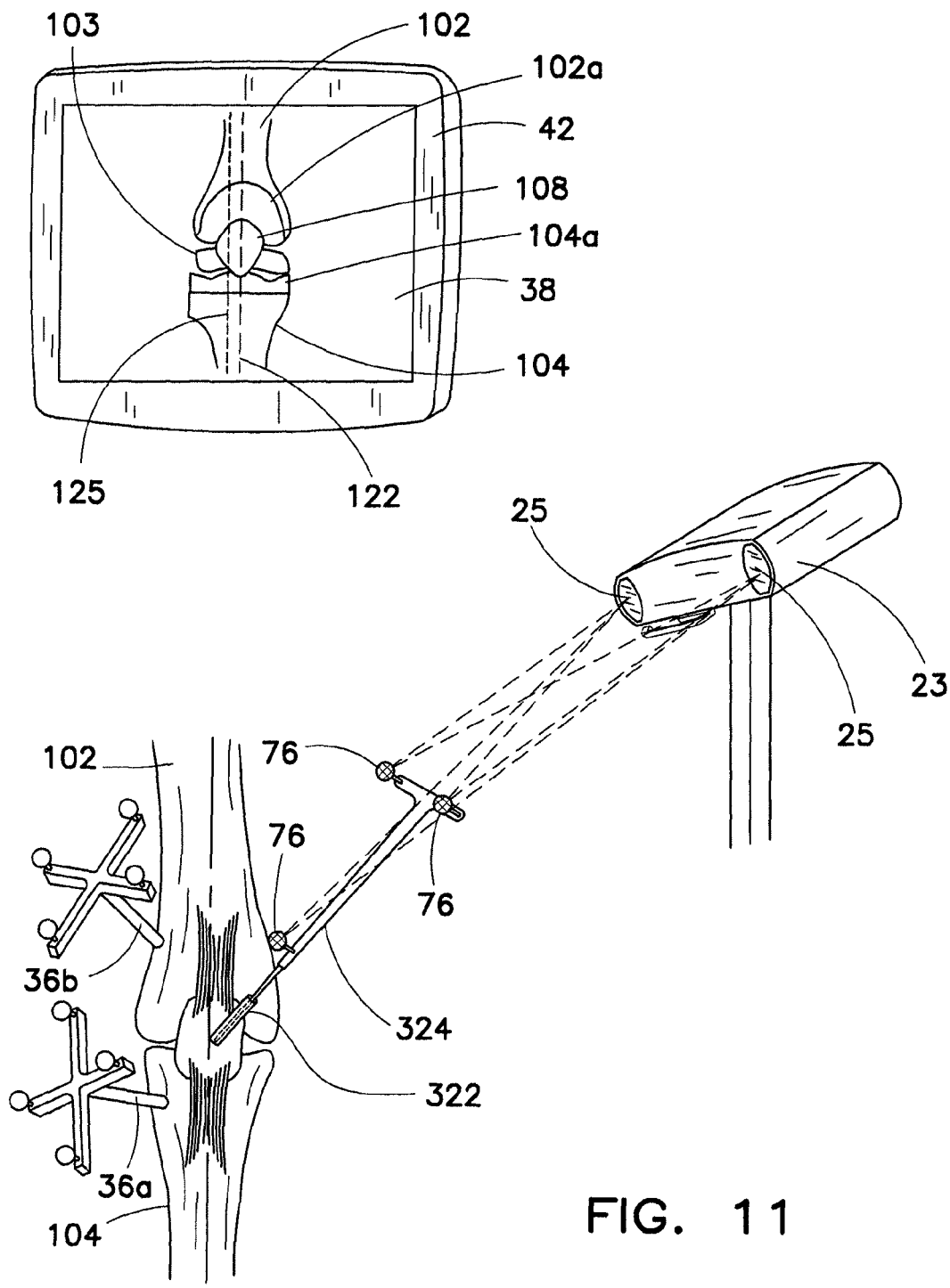
FIG. 11 is a partial fragmentary perspective view illustrating yet another patella tracking procedure in accordance with the present teachings.

Moving now to FIG. 11, yet another embodiment in accordance with the present teachings is shown. In this embodiment, a probe array guide 322 is affixed to the patella 108 along the femoral-tibial axis 122. More particularly, the surgeon determines the femoral-tibial mechanical axis 122 by touching/acquiring the surgical probe array 324 against the surface of the femur and tibia at two individual locations that together form a line defining the respective femoral and tibial mechanical axes. The surgical probe array 324 includes markers 76, which are identified and tracked by cameras 25 of the optical locator 23. As the surgeon positions the surgical probe array 324 against the femur and tibia, the tracking system locates and tracks the markers 76 in real-time and detects their position in space by using triangulation methods. To accomplish this, the tracking system detects the location of the surgical probe array 324 as it is positioned relative to the femur 102 and the tibia 104 by referencing the position of the markers 76 as they move with respect to the reference arrays 36b and 36a, which are fixably attached to the femur and tibia, respectively. After the femoral-tibial mechanical axis 122 is acquired by the surgical probe array 324, a representation is then shown as a computer display image 38 on the computer monitor 42 for use by the surgeon during the surgical procedure.

After the femoral-tibial mechanical axis 122 is determined, the surgeon drills the probe array guide 322 into the patella at a center point along the femoral-tibial mechanical axis 122. Once affixed to the patella, the probe array guide can be used to hold the tip of the probe array 324 against the patella 108 as the leg is moved between flexion and extension and thereby indicating how the leg is tracking with respect to the femoral-tibial mechanical axis 122. In other words, as the surgeon moves the leg between flexion and extension, the computer display image 38 on the computer monitor 42 shows the actual axial path 125 the leg is moving with respect to the femoral-tibial axis 122. Based on the alignment of these two axes (i.e., 122, 125), the surgeon 21 can decide whether further alignment is needed. For instance, the surgeon can correct a misalignment by adjusting the positioning of one or more of the surgical components, such as the femoral component, which is configured to articulate against the surface of the patella trial button during movement of the leg.

While various illustrative embodiments incorporating the principles of the present teachings have been disclosed hereinabove, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain and which fall within the limits of the appended claims.

What is claimed is:

1. A surgical navigation system for tracking movement of a patella as a leg is moved through a range of motion during a surgical procedure, comprising:

a frame having a first surface spaced apart from and at least partially parallel to a second surface, wherein the first and second surfaces are bridged by a third surface at a first end of the frame, wherein the first, second and third surfaces together cooperate to define a substantially C-shaped space that is adapted to receive and at least partially encase the patella during the surgical procedure, and wherein at least one of the first, second and third surfaces is configured to directly contact the patella; and a reference array extending from one of the first and second surfaces of the frame, the reference array having first, second and third markers detectable by the surgical navigation system when exposed to a measurement field thereof; and wherein the surgical navigation system is configured to detect a path traveled by the patella by determining the relative location of the reference array as the leg is moved through a range of motion.

2. The surgical navigation system of claim 1, further comprising a monitor for displaying an image of the path traveled by the patella, the image further being configured to display a femoral-tibial mechanical axis.

3. The surgical navigation system of claim 1, wherein the surgical navigation system is configured to detect the path traveled by the patella by determining the relative location of the reference array as the leg is moved between flexion and extension.

4. The surgical navigation system of claim 1, further comprising a patella trial component associated with the frame.

5. The surgical navigation system of claim 4, wherein the frame includes a series of openings for forming holes in the patella.

6. The surgical navigation system of claim 4, wherein the patella trial component includes a series of prongs adapted to fit into the formed holes and to retain the patella against the frame.

7. The surgical navigation system of claim 6, wherein the formed holes are configured to accommodate a patella implant upon removal of the patella trial component from the patella.

* * * * *